(12) United States Patent
Ben Oren et al.

(10) Patent No.: US 9,730,756 B2
(45) Date of Patent: *Aug. 15, 2017

(54) HYBRID CATHETER FOR VASCULAR INTERVENTION

(75) Inventors: Ilan Ben Oren, Modi'in (IL); Yifat Ben Oren Tamir, Modi'in (IL)

(73) Assignee: Eximo Medical Ltd., Modi'in (IL)

( * ) Notice: Subject to any disclaimer, the term of this patent is extended or adjusted under 35 U.S.C. 154(b) by 548 days.

This patent is subject to a terminal disclaimer.

(21) Appl. No.: 14/001,633

(22) PCT Filed: Feb. 23, 2012

(86) PCT No.: PCT/IL2012/000088
§ 371 (c)(1),
(2), (4) Date: Oct. 17, 2013

(87) PCT Pub. No.: WO2012/114333
PCT Pub. Date: Aug. 30, 2012

(65) Prior Publication Data
US 2014/0031800 A1    Jan. 30, 2014

Related U.S. Application Data

(60) Provisional application No. 61/446,145, filed on Feb. 24, 2011, provisional application No. 61/521,523, filed on Aug. 9, 2011.

(51) Int. Cl.
*A61B 18/22* (2006.01)
*A61B 17/32* (2006.01)
(Continued)

(52) U.S. Cl.
CPC .......... *A61B 18/22* (2013.01); *A61B 1/00087* (2013.01); *A61B 1/3137* (2013.01);
(Continued)

(58) Field of Classification Search
CPC . A61B 18/22; A61B 17/320016; A61B 18/24; A61B 18/245; A61B 17/32002
See application file for complete search history.

(56) References Cited

U.S. PATENT DOCUMENTS

| 4,832,024 A | 5/1989 | Boussignac |
| 4,844,062 A | 7/1989 | Wells |

(Continued)

FOREIGN PATENT DOCUMENTS

| CA | 1326800 | 2/1994 |
| CN | 1049287 | 2/1991 |

(Continued)

OTHER PUBLICATIONS

Alexander (1991) Tissue pathologies uncovered by spectral analysis. J Clin Laser Med Surg 9(4): 238-241.

(Continued)

*Primary Examiner* — Lynsey Crandall
*Assistant Examiner* — Dacheng Xie
(74) *Attorney, Agent, or Firm* — Rodney J. Fuller; Booth Udall Fuller, PLC

(57) ABSTRACT

A catheter for debulking of an undesired deposit from an inner surface of at least one of a blood vessel wall and a stent located in a blood vessel, the catheter having a tip section comprising: circumferentially-directed laser optics; and a circular-action cutter, wherein said circumferentially-directed laser optics is configured to transmit laser radiation for modifying an area of the undesired deposit thereby preparing said area for penetration of said cutter, wherein said cutter is configured to cut through said modified area and thereby debulk at least a part of the undesired deposit. In addition, a catheter for pacemaker and ICD (Implantable Cardioverter Defibrillator) lead extraction is disclosed.

13 Claims, 10 Drawing Sheets

(51) Int. Cl.
*A61B 1/00* (2006.01)
*A61B 1/313* (2006.01)
*A61B 18/24* (2006.01)
*A61B 17/00* (2006.01)
*A61B 17/22* (2006.01)
*A61B 90/00* (2016.01)
*A61B 90/30* (2016.01)

(52) U.S. Cl.
CPC ...... *A61B 17/320016* (2013.01); *A61B 18/24* (2013.01); *A61B 18/245* (2013.01); *A61B 17/32002* (2013.01); *A61B 2017/00269* (2013.01); *A61B 2017/00398* (2013.01); *A61B 2017/00867* (2013.01); *A61B 2017/22082* (2013.01); *A61B 2018/2211* (2013.01); *A61B 2090/306* (2016.02); *A61B 2090/3614* (2016.02)

(56) References Cited

U.S. PATENT DOCUMENTS

| | | | |
|---|---|---|---|
| 4,955,882 A * | 9/1990 | Hakky | A61B 17/32002 606/14 |
| 4,966,596 A | 10/1990 | Kuntz | |
| 4,979,939 A | 12/1990 | Shiber | |
| 5,026,366 A | 6/1991 | Leckrone | |
| 5,029,588 A | 7/1991 | Yock | |
| 5,053,033 A | 10/1991 | Clarke | |
| 5,196,004 A | 3/1993 | Sinofsky | |
| 5,222,966 A | 6/1993 | Perkins | |
| 5,312,399 A | 5/1994 | Hakky | |
| 5,498,258 A | 3/1996 | Hakky | |
| 5,536,248 A | 7/1996 | Weaver | |
| 5,571,098 A | 11/1996 | Domankevitz | |
| 5,653,696 A * | 8/1997 | Shiber | A61B 17/22012 604/267 |
| 5,951,543 A | 9/1999 | Brauer | |
| 6,027,450 A | 2/2000 | Brown | |
| 6,106,515 A | 8/2000 | Winston | |
| 6,206,898 B1 | 3/2001 | Honeycutt et al. | |
| 6,454,790 B1 | 9/2002 | Neuberger | |
| 6,539,944 B1 * | 4/2003 | Watson | A61B 18/20 128/898 |
| 6,673,064 B1 | 1/2004 | Rentrop | |
| 6,673,065 B1 | 1/2004 | Veligdan | |
| 6,845,193 B2 | 1/2005 | Loeb | |
| 6,962,585 B2 | 11/2005 | Poleo | |
| 7,186,252 B2 | 3/2007 | Nobis | |
| 7,247,162 B1 | 7/2007 | Thornton | |
| 7,479,147 B2 | 1/2009 | Honeycutt et al. | |
| 7,524,289 B2 | 4/2009 | Lenker | |
| 7,572,254 B2 | 8/2009 | Hebert | |
| 7,699,790 B2 | 4/2010 | Simpson | |
| 7,811,281 B1 | 10/2010 | Rentrop | |
| 8,657,785 B2 | 2/2014 | Torrance et al. | |
| 8,702,773 B2 | 4/2014 | Keeler | |
| 8,728,066 B2 | 5/2014 | Shadduck et al. | |
| 9,050,127 B2 | 6/2015 | Bonnette et al. | |
| 9,295,373 B2 | 3/2016 | Torrance et al. | |
| 9,345,510 B2 | 5/2016 | Patel et al. | |
| 9,456,872 B2 | 10/2016 | Hendrick et al. | |
| 2002/0016624 A1 | 2/2002 | Patterson | |
| 2003/0181847 A1 | 9/2003 | Bruno-Raimondi | |
| 2003/0181938 A1 | 9/2003 | Roth | |
| 2005/0187537 A1 | 8/2005 | Loeb | |
| 2005/0251116 A1 | 11/2005 | Steinke | |
| 2006/0095059 A1 | 5/2006 | Bleich | |
| 2006/0253112 A1 * | 11/2006 | Suarez | A61B 18/20 606/9 |
| 2007/0208400 A1 | 9/2007 | Nadkarni | |
| 2007/0270688 A1 * | 11/2007 | Gelbart | A61B 5/053 600/427 |
| 2008/0119869 A1 * | 5/2008 | Teague | A61B 17/221 606/127 |
| 2008/0275445 A1 | 11/2008 | Kelly | |
| 2009/0018603 A1 | 1/2009 | Mitelberg | |
| 2009/0125007 A1 * | 5/2009 | Splinter | A61B 18/24 606/15 |
| 2009/0234344 A1 * | 9/2009 | Lavender | A61B 18/203 606/10 |
| 2009/0234378 A1 * | 9/2009 | Escudero | A61B 17/320758 606/180 |
| 2009/0247823 A1 | 10/2009 | Yamamoto | |
| 2010/0125253 A1 | 5/2010 | Olson | |
| 2010/0198240 A1 | 8/2010 | Simpson | |
| 2010/0198247 A1 | 8/2010 | Chang | |
| 2010/0286791 A1 * | 11/2010 | Goldsmith | A61B 17/12022 623/23.7 |
| 2010/0312263 A1 | 12/2010 | Moberg | |
| 2011/0213446 A1 | 9/2011 | Tucek | |

FOREIGN PATENT DOCUMENTS

| | | |
|---|---|---|
| CN | 2713994 | 8/2005 |
| EP | 0341943 | 11/1989 |
| EP | 2226031 | 9/2010 |
| WO | 9834673 | 8/1998 |
| WO | 0245601 | 6/2002 |
| WO | 2004021886 | 3/2004 |
| WO | 2004043280 | 5/2004 |
| WO | 2012114334 | 8/2012 |
| WO | 2014/118738 | 8/2014 |

OTHER PUBLICATIONS

Cummings et al., (2004) Gastric bypass for obesity: mechanisms of weight loss and diabetes resolution. J Clin Endocrinol Metab 89(6): 2608-15.

Fleischer and Sharma (2009) Endoscopic Ablation of Barrett's Esophagus Using the Halo® System. Dig Dis 26(4): 280-284.

Fleischer and Sharma, Endoscopic Ablation of Barrett's Esophagus Using the HALO® System. Mönkemüller K, Wilcox CM, Muñoz-Navas M (eds):Interventional and Therapeutic Gastrointestinal Endoscopy. Front Gastrointest Res. Basel, Karger, 2010, vol. 27, pp. 140-146.

Grundfest et al., (1985) Pulsed ultraviolet lasers and the potential for safe laser angioplasty. Am J Surg 150(2): 220-226.

Jackson (2009) High-power and highly efficient diode-cladding-pumped holmium-doped fluoride fiber laser operating at 2.94 microm. Opt Lett 34(15): 2327-2329.

Jackson et al., (2007) Directly diode-pumped holmium fiber lasers. Opt Lett 32(17): 2496-2498.

Litvack et al., (1988) Pulsed laser angioplasty: wavelength power and energy dependencies relevant to clinical application. Lasers Surg Med 8(1): 60-65.

Murphy-Chutorian et al., (1985) Selective absorption of ultraviolet laser energy by human atherosclerotic plaque treated with tetracycline. Am J Cardiol 55(11): 1293-1297.

Pories and Albrecht (2001) Etiology of type II diabetes mellitus: role of the foregut. World J Surg 25(4): 527-31.

Pories et al., (2011) The surgical treatment of type two diabetes mellitus. Surg Clin North Am 91(4): 821-36.

Ronkainen et al., (2005) Prevalence of Barrett's esophagus in the general population: an endoscopic study. Gastroenterology 129(6): 1825-1831.

Rubino and Gagner (2002) Potential of surgery for curing type 2 diabetes mellitus. Ann Surg 236(5): 554-9.

Rubino and Marescaux (2004) Effect of duodenal-jejunal exclusion in a non-obese animal model of type 2 diabetes: a new perspective for an old disease. Ann Surg 239(1): 1-11.

Rubino et al., (2006) The mechanism of diabetes control after gastrointestinal bypass surgery reveals a role of the proximal small intestine in the pathophysiology of type 2 diabetes. Ann Surg 244(5): 741-9.

Schwarzwälder and Zeller (2010) Debulking procedures: potential device specific indications. Tech Vasc Interv Radiol 13(1): 43-53.

(56) References Cited

OTHER PUBLICATIONS

Sikorska and Pan (2004) The effect of waveguide material and shape on acoustic emission transmission characteristics, part 1: traditional features. J Acoustic Emission 22: 264-273.
Skorczakowski et al., (2010) Mid-infrared Q-switched Er:YAG laser for medical applications. Laser Physics Letters 7 (7): 498-504.
Verdam et al., (2012) An Update on Less Invasive and Endoscopic Techniques Mimicking the Effect of Bariatric Surgery. J Obes 2012: 597871.
Wang et al., (2013) Total transmission and total reflection of acoustic wave by zero index metamaterials loaded with general solid defects. Journal of Applied Physics 114(19): 194502.

* cited by examiner

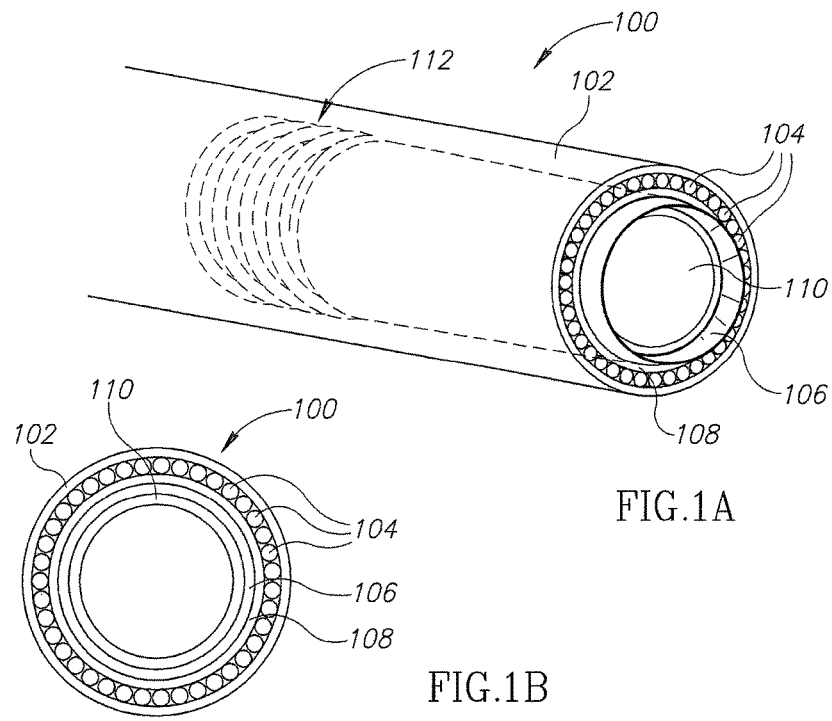
FIG.1A
FIG.1B
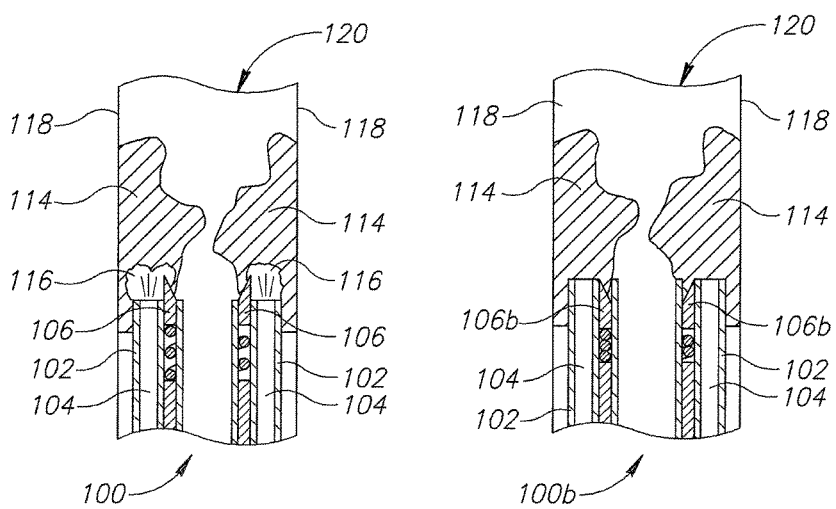
FIG.1C

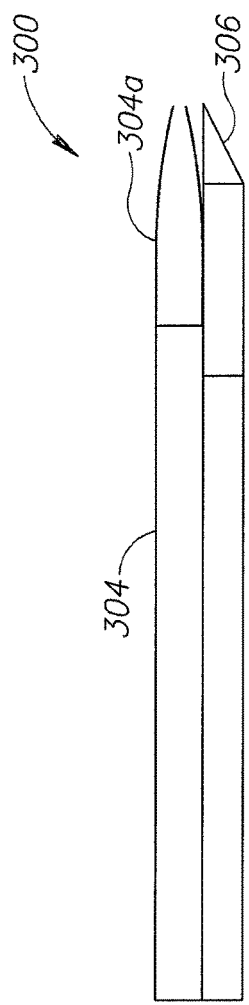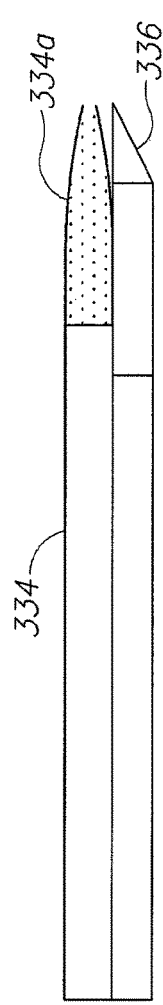
FIG.3A  FIG.3B

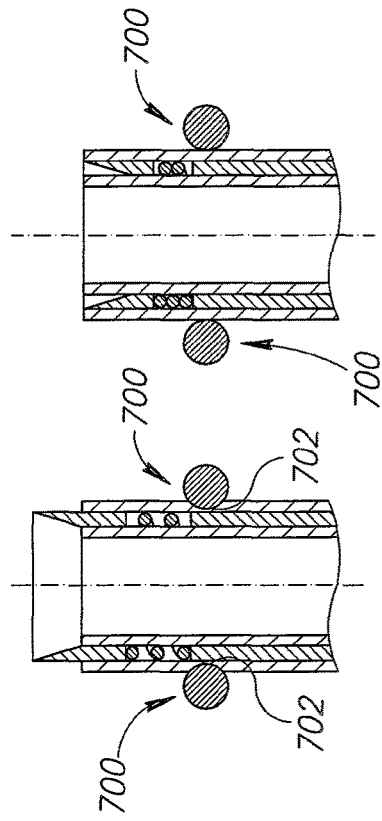
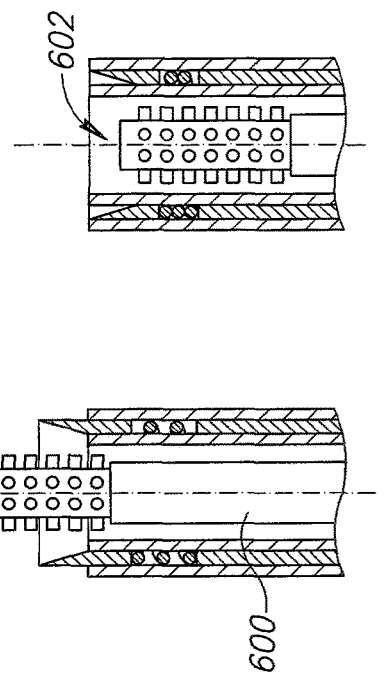
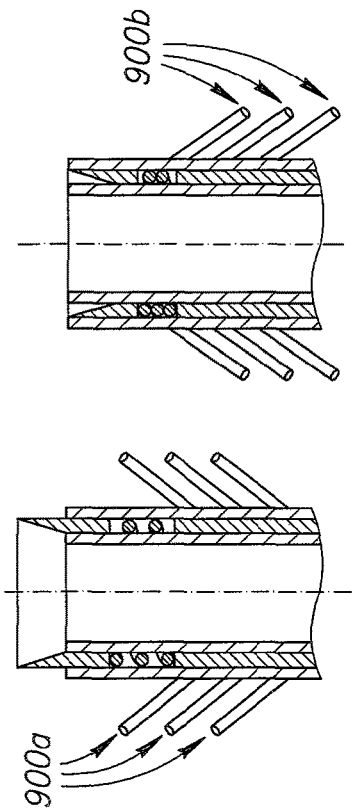
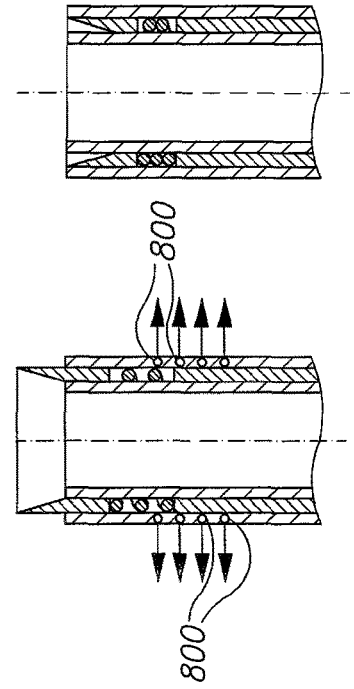

HYBRID CATHETER FOR VASCULAR INTERVENTION

RELATED APPLICATION DATA

This application is a U.S. National Stage of International Application No. PCT/IL2012/000088, filed Feb. 23, 2012, which claims the benefit of U.S. Provisional Application No. 61/446,145, filed Feb. 24, 2011, and U.S. Provisional Application No. 61/521,523, filed Aug. 9, 2011, the contents of each of which are herein expressly incorporated by reference for all purposes in their entireties.

FIELD OF THE INVENTION

The invention relates to a hybrid catheter for vascular or other interventions.

BACKGROUND OF THE INVENTION

Peripheral and arterial vascular diseases are a common problem which may directly lead to morbidity and death. In the U.S. alone it is estimated that over 4 million people suffer from peripheral artery disease which, in severe cases, is treated with surgery or even amputation.

Flat lesions represent a significant challenge in gastroenterology. Removing of sessile and flat polyps, which may be associated with high risk for malignancy, requires, in most cases, usage of different techniques than those used for removing common polyps. These techniques may lead to the referral of patients to surgery instead of removal by the gastroenterologist. Other challenging lesions are nonpolypoid colorectal neoplasms (NP-CRNs). Barrett's esophagus is another common chronic condition. The prevalence in the U.S. population is estimated to be in the range of 1-2% of the adult population. Barrett's esophagus condition may lead to violent esophageal cancer, which is said to result in over 12,000 deaths per year in the U.S. alone and around 100,000 in China.

Laser and Mechanical Based Solutions for Angioplasty, Atherectomy and Thrombectomy:

The current state of the art in laser ablation technology for vascular intervention is based on use of an Excimer lasers with dedicated catheters such as Spectranetics' CVX-300® laser and TURBO-Booster® catheter. These technologies are described, for example, in U.S. Pat. Nos. 6,673,064, 7,811,281 and 7,572,254. Due to technical and safety considerations, the excimer laser used, generally, is often a Xenon Chloride laser operative at 308 nm with pulse widths in the range of 100 nanoseconds. These technologies are not ideal and have some limitations. For example, when dealing with heavy calcified plaques, there is a risk of perforation and damage from debris/plaque fragments. Therefore, the procedure requires a complex, large and costly system and the length of the procedure is quite significant in a manner that seems to limit its wide clinical utility. In addition, the technique had difficulties in treatment of large vessels such as SFA (Superficial Femoral Artery) which is very important in management of peripheral artery disease (PAD) wherein vessels larger than 4-5 mm in diameter and long lesions have to be treated.

One of the reasons for the length of the process is that even one of the most advanced solutions, combining the TURBO-Booster® and the TURBO Laser Elite catheters, may require a number of steps starting with atherectomy to create an initial pilot channel through the whole lesion, for example using the laser catheter alone, and only at later stages the laser catheter is loaded into the introducer sheath. The use of the catheter is based on several passages, each after rotation of the catheter. See Schwarzwälder U, Zeller T, Tech Vasc Interv Radiol. 2010 March; 13(1):43-53.

Additional limitations of this solution include ineffective removal of arterial debris and high risk of artery walls injury, as mentioned, for example, in U.S. Pat. No. 6,962,585:

"An Excimer Laser Coronary Angioplasty system and procedure offered by Spectranetics of Colorado Springs, Colo., involves the insertion into an artery of a laser catheter containing a bundle of optical fibers and a stent with a guide wire. The laser catheter is advanced in the artery until the guide wire crosses a blockage, at which time bursts of ultraviolet (cool) laser light is transmitted through the fiber optic fibers to open a hole in the blockage. Thereafter, an x-ray contrast dye is injected into the blood stream to determine the extent to which the artery has been opened. This procedure does not remove substantial amounts of blockage, because ultra violet radiation is too cool to melt the blockage. Rather, a hole is blasted through the blockage to accommodate the admission of a stent. While the catherization system includes a filter, the filter is not sufficient to catch all debris which may flow downstream.

Such prior systems have failed because they have not effectively removed arterial blockage from the artery walls, and have not effectively removed arterial debris from the artery once the arterial blockage has been dislodged. In addition, such prior systems have not adequately protected the artery walls from physical or thermal injury. Further, many of the prior art devices embody numerous parts which tend to fail or shatter in a high temperature/high vacuum environment." (id, p. 1, ln. 19)

An alternative approach using IR laser for thermal heating of a tip used to cut the plaques to be removed with suction is disclosed in U.S. Pat. No. 6,962,585. This approach may suffer from the limitations and risk involved with plaque removal based on non-selective heating. The approach proposed in this case is to use arterial guards in the outer part of the catheter that may limit the passage of the catheter and avoid getting closer to the walls. Other attempts to use thermal effects include a hybrid thermal probe, wherein most of the laser energy (Argon or Nd:YAG) is used to heat the hot tip in the catheter, and part of it escapes as laser light. Clinical results were not satisfactory to enable routine clinical use.

Additional prior approaches include use of a laser to core the plaque and use of mechanical means to "ingest" and remove the plaque. See, for example, U.S. Pat. No. 4,979,939. In Canadian Patent No. 1,326,800 a fiber is introduced to create an opening through which the distal rotary is introduced and the second fiber is used to vaporize the material collected by the blade. U.S. Patent Application Publication No. 2010/0125253 discloses a dual tip catheter for treating chronic total occlusions through which a fiber may be introduced.

In view of the complexity and limitations of the laser based technologies, the systems based on excimer laser have had limited spread in clinical use, and alternative mechanical methods for atherectomy have been developed, for example, wherein the plaques are "shaved" (the EV3 product), "drilled" (the Pathway product) or "sanded" with a rotating diamond coated brush (the CSI product). Each of these techniques may often suffer from inherent limitations such as procedure length, injury to the blood vessels, difficulty in dealing with calcified plaques in certain cases and, on the contrary, dealing with soft plaque (see Schwarzwälder U, Zeller T, Tech Vasc Interv Radiol. 2010 March; 13(1):43-53) or discarding of plaque material into the blood stream.

It should be noted that it is assumed by experts in the area that injury of healthy tissue and the characteristics of the tissue after plaque is removed may affect the healing (and initial hyperplasia) and the rate of restenosis which seems to be a limitation of some of the above-mentioned techniques. Furthermore, in view of the limited capabilities to remove plaque with many prior techniques, their current utility is limited mainly for use in conjunction with low pressure balloon angioplasty used after plaque is partially removed. The balloon then opens the vessel with the remaining plaque material.

The need to deal with complete or partial blockage in vessels applies also to artificial grafts, such as those implanted in the legs for bypass, for hemodialyisis access and more.

In-stent-restenosis. It is known in the art that in a significant percentage of the patients that underwent stent implantation, restenosis occurs within a few years after implantation. This is a major issue with bare-metal stents (BMS) and even introduction of drug eluting stents (DES) that show a robust decrease of restenosis still does not completely solve the problem.

Acute blockage of vessels. There is also a need for tools that quickly open blood vessels in patients that suffer from ischemic stroke (caused by blockage of a blood vessel) or in heart attacks with the minimal risk of perforation.

Removal of pacemaker and defibrillator leads. Presently there is a growing need to remove pacemaker and defibrillators leads in a subset of patients due to several reasons such lead fracture, abrasion of the insulation causing shorting and infections. Approximately 5 million leads are implanted worldwide and it is estimated that 4-7% will have to be removed at certain time point. It is estimated that over 100,000 leads were extracted in the US, and Europe in 2010.

There are several approaches to remove transvenously introduced ICD leads. If leads have been in place for only a short period, they can frequently be removed by simple traction. After the leads are in place for long time scar tissue may withholds the leads during traction, the force applied to the leads is limited by the tensile strength of the insulation and conductor coils, therefore locking stylets and sheaths are used to enable a more forceful tension, but successful lead removal can still be very problematic when the leads is attached to sensitive tissue such myocardial wall. In severe cases lead extraction may require open surgery. The Spectranetics Excimer Laser and Cook Medical's Evolution products are currently used for lead removal using transcatheter techniques. The "debulking" of the lead using an excimer laser has yielded good clinical results but requires a large and expensive laser that does not allow wide use in any cardiology unit and a relative long learning curve is required.

There is a need for an effective and safe solution for removal of pacemakers and defibrillator leads in patients.

Management of Barrette's Esophagus. Barrett's Esophagus (BE) is a common disorder that is a major risk factor for esophagus cancer. The prevalence of the disorder is estimated to be in the range of 1-2%. See Ronkainen J, Aro P, Storskrubb T, et al. (December 2005) "Prevalence of Barrett's esophagus in the general population: an endoscopic study", Gastroenterology 129 (6): 1825-31. The range of severity can vary from early stage to different grades of dysplasia to cancer. Prior attempts to manage this condition with Argon coagulation yielded controversial results. Alternative methods are based on RF ablation (RFA) (Halo® System), photodynamic therapy (PDT), cryo, thermal therapy or surgery as endoscopic mucosal resection (EMR). No method resulted in wide clinical acceptance that can enable routine use in a broad population instead of "waiting and watching" in early stages in the disease and specific therapies including esophagus resection in more sever conditions.

Furthermore, as no single technique has been established as the preferred method, a combination of techniques is used in certain cases. For example, there may be a consensus that RFA is useful for patients with BE and high-grade dysplasia (HGD), BE and intramucosal carcinoma as an adjunct to endoscopic mucosal resection (EMR). The use of RFA for BE with low-grade dysplasia (LGD) or intestinal metaplasia is not clearly established, see David E. Fleischer_Virender K. Sharma, Interventional and Therapeutic Gastrointestinal Endoscopy. Front Gastrointest Res. Basel, Karger, 2010, vol 27, pp 140-146. On the other hand, EMR sometimes does not allow removing all of the Barrett's lining but can be successful in removing a small cancer or a localized area of high-grade dysplasia. Because it does not remove all of the Barrett's lining, the Barrett's lining left behind can develop other areas of high-grade dysplasia or cancer. Therefore, EMR is sometimes combined with photodynamic therapy in an attempt to remove remaining Barrett's tissue or with RF ablation. Conversely, several photodynamic therapy studies have also reported that a few patients have a situation in which the Barrett's lining does not completely go away but is still there, underneath the new normal-appearing squamous lining (and detected when biopsy is performed that shows that small areas of Barrett's lining are still there underneath the new squamous lining.) In such a case, another course of treatment with another technique might be beneficial.

Complications of the current available techniques include perforations (making a hole in the esophagus), bleeding, strictures, light sensitivity in PDT and even death.

Removal of challenging lesions in intestine and stomach. Some of the polyps and adenomas (benign tumors) detected with an increasing percent in colonoscopy, with different imaging techniques, do not have a conventional "pedunculated" shape. Polyps that are not attached to the surface by a narrow elongated stalk are called sessile. Other polyps are not significantly elevated from the adjacent mucosa are called flat. Accordingly, the removal of large sessile and flat colorectal is more difficult than removal of pedunculated polyps and in many cases require using special endoscopy techniques to avoid perforation.

These lesions may be associated with high clinical risk. The incidence of cancer with submucosal invasion appears to be higher in flat-type lateral spreading tumors.

Endoscopic Mucosal Resection (EMR) is becoming the standard technique for resection of large sessile and flat colorectal lesions. For the more challenging lesions, Endoscopic Submucosal Dissection (ESD) can be used. ESD can be performed using a viscous injection solution for sustained submucosal lifting, a diathermy knife, and a plastic hood to help retract the polyp as it is dissected away from the muscularis propria.

Although these techniques are feasible anywhere in the colon, currently these techniques are technically challenging and time consuming and ESD carries a relatively high rate of major complication. Laser ablation is usually not perceived as an adequate solution for this application, as there is a need to assure adequate (i.e. complete) removal of pathological tissue and preferably to collect resected samples for histological analysis There is thus an unmet need in the art for devices, systems and methods that would allow efficient and effective vascular interventions as well as removal of challenging lesions in the gastroenterology (GI) track (mainly in colon and stomach) and Barrett's esophagus management.

Removal of challenging lesions in gynecology and urology. There is a need for effective and safe tools for removal of pathological tissue in gynecology (cervical uterus) and urology (urinary bladder, prostate), wherein the depth of resection can be controlled while risk of perforation and bleeding is minimized.

SUMMARY OF THE INVENTION

There is provided, in accordance with some embodiments, a catheter for debulking of an undesired deposit from an inner surface of at least one of a blood vessel wall and a stent located in a blood vessel, the catheter having a tip section comprising: circumferentially-directed laser optics; and a circular-action cutter, wherein said circumferentially-directed laser optics is configured to transmit laser radiation for modifying an area of the undesired deposit thereby preparing said area for penetration of said cutter, wherein said cutter is configured to cut through said modified area and thereby debulk at least a part of the undesired deposit.

There is further provided, in accordance with some embodiments, a method for debulking of undesired deposit from an inner surface of at least one of a blood vessel wall and a stent located in a blood vessel, the method comprising, using a catheter: irradiating an area of the undesired deposit using a circumferentially-directed laser optics, thereby modifying said area; and cutting through said modified area using a circular-action cutter, thereby debulking at least a part of said undesired deposit.

There is further provided, in accordance with some embodiments, a catheter for debulking of an undesired deposit from an inner surface of at least one of a blood vessel wall and a stent located in a blood vessel, the catheter having a tip section comprising: a first wall having a circular cross section and having a sharp distal edge; and a plurality of optical fibers located along the surface of said first wall, wherein said plurality of optical fibers are configured to transmit laser radiation configured to modify the undesired deposit and thereby preparing the undesired deposit for penetration of said sharp distal edge of said first wall, wherein said first wall is configured to cut through said modified undesired deposit and thereby debulk at least a part of the undesired deposit.

There is further provided, in accordance with some embodiments, a method for debulking of undesired deposit from an inner surface of at least one of a blood vessel wall and a stent located in a blood vessel, the method comprising, using a catheter: using a catheter having a plurality of optical fibers, transmitting laser radiation towards an undesired deposit thereby modifying the undesired deposit and preparing the undesired deposit for penetration of a sharp distal edge of a catheter's wall; and advancing the catheter and cutting through the modified undesired deposit thereby debulking at least a part of said undesired deposit.

There is further provided, in accordance with some embodiments, a catheter for pacemaker and ICD (Implantable Cardioverter Defibrillator) lead extraction, the catheter having a tip section comprising: a first wall having a circular cross section and having a sharp distal edge; and a plurality of optical fibers located along the surface of said first wall, wherein said plurality of optical fibers are configured to transmit laser radiation configured to modify the tissue surrounding the lead thereby preparing the tissue for penetration of said sharp distal edge of said first wall, wherein said first wall is configured to cut through said modified tissue and thereby detach the lead from the tissue.

There is further provided, in accordance with some embodiments, a method for pacemaker and ICD (Implantable Cardioverter Defibrillator) lead extraction, the method comprising: using a catheter having a plurality of optical fibers, transmitting laser radiation towards a tissue surrounding the lead thereby modifying the tissue and preparing the tissue for penetration of a sharp distal edge of a catheter's wall; and advancing the catheter over the lead by cutting through the modified tissue surrounding the lead and thereby detach the lead from the tissue.

There is further provided, in accordance with some embodiments, a catheter for pacemaker and ICD (Implantable Cardioverter Defibrillator) lead extraction, the catheter having a tip section comprising: circumferentially-directed laser optics; and a circular-action cutter, wherein said circumferentially-directed laser optics is configured to transmit laser radiation for modifying the tissue surrounding the lead thereby preparing said tissue for penetration of said cutter, wherein said cutter is configured to cut through said modified tissue and thereby detach the lead from the tissue.

There is further provided, in accordance with some embodiments, a device for detaching undesired tissue from an inner wall of a body cavity, the device having a tip section in a shape of a cylinder's sector, the tip section comprising: a plurality of optical fibers located along an inner surface of the tip section and configured to transmit laser radiation to the undesired tissue; and a cutter having a shape of a cylinder's sector located inwardly and/or outwardly to the plurality of optical fibers, wherein said cutter is configured to cut through the undesired tissue and thereby detach at least a part of the undesired tissue from the inner wall of the body cavity.

There is further provided, in accordance with some embodiments, a method for detaching undesired tissue from an inner wall of a body cavity, the method comprising: using a plurality of optical fibers, transmitting laser radiation to an area of said undesired tissue, thereby modifying said area; and cutting through said modified area using a cutter, thereby detaching at least a part of said undesired tissue.

In some embodiments, an angle between said device and said endoscope's longitudinal axis is adjustable according to a required depth of peeling of said undesired tissue.

In some embodiments, cutting comprises rotatably cutting using a blade rotatable along an inner surface of a cylindrical tip section of the catheter.

In some embodiments, cutting comprises rotatably cutting using an annular blade.

In some embodiments, cutting further comprising vibrating said cutter.

In some embodiments, detaching the undesired tissue comprises peeling of the undesired tissue.

In some embodiments, mechanically weakening comprises ablation of said tissue.

In some embodiments, modifying said area of said undesired deposit comprises mechanically weakening said area.

In some embodiments, modifying said tissue comprises mechanically weakening said area.

In some embodiments, modifying said undesired deposit comprises mechanically weakening said area.

In some embodiments, said circumferentially-directed laser optics comprises a plurality of optical fibers located along an inner surface of the cylindrical tip section.

In some embodiments, said circumferentially-directed laser optics and said circular-action cutter are configured to operate simultaneously.

In some embodiments, said circumferentially-directed laser optics and said circular-action cutter are configured to operate intermittently.

In some embodiments, said cutter comprises a blade rotatable along said inner surface of said cylindrical tip section, inwardly or outwardly to said plurality of optical fibers.

In some embodiments, said cutter comprises an annular blade located along an inner or an outer surface of the cylindrical tip section, inwardly or outwardly to said plurality of optical fibers.

In some embodiments, said cutter is configured to have two positions, in a first position, the cutter extends further from a distal end of the tip section, and in a second position the cutter is retracted towards a proximal part of the tip section.

In some embodiments, said cutter is configured to shift from the first position to the second position when a force above a predetermined value is applied on said cutter.

In some embodiments, said cutter is configured to shift from the first position to the second position upon indication of a force applied on said cutter being above a predetermined value.

In some embodiments, said cutter is configured to shift from the first position to the second position when a force above a predetermined value is applied on said cutter.

In some embodiments, said cutter is configured to vibrate.

In some embodiments, said cutter is said catheter's wall, wherein said wall has sharp distal edges.

In some embodiments, said drug comprises: Elutax®, SeQuent®, Cotavance™ with Paccocath® coating technology, TADD (from Caliber Therapeutics, Inc.), Advance® 18PTX®, DIOR®, IN.PACT™ Amphirion, Coroxane or any combination thereof.

In some embodiments, said laser is a diode pump Holmium Fiber laser.

In some embodiments, said laser is a pulse laser with emitting radiation in the range of 2.8-3-microns.

In some embodiments, said laser is a pulse Thulium laser

In some embodiments, said laser is a pulse Thulium fiber laser.

In some embodiments, said laser is a Er:YAG laser

In some embodiments, said laser is a fiber laser configured to emit at 2.8-3 microns.

In some embodiments, said laser is a pulsed laser.

In some embodiments, said laser is a solid state triple Nd:YAG laser.

In some embodiments, said laser radiation is pulsed radiation.

In some embodiments, said one or more lead retraction elements are configured to grab the lead only when the catheter is moving outside of the body.

In some embodiments, said one or more lead retraction elements comprise a balloon.

In some embodiments, said plurality of optical fibers and said cutter are configured to operate simultaneously.

In some embodiments, said plurality of optical fibers and said cutter are configured to operate intermittently.

In some embodiments, said plurality of optical fibers are configured to modify an area of the undesired tissue thereby preparing said area for penetration of said cutter, wherein said cutter is configured to cut through said modified area and thereby detach at least a part of the undesired tissue.

In some embodiments, said plurality of optical fibers are located along an inner surface of said first wall.

In some embodiments, said plurality of optical fibers are located along an outer surface of said first wall.

In some embodiments, said plurality of optical fibers comprise one or more optical fibers having a proximal diameter larger than their distal diameter.

In some embodiments, said second wall comprises a sharp distal edge.

In some embodiments, said tip section is cylindrical.

In some embodiments, said tip section is expandable.

In some embodiments, the catheter further comprises a drug eluting balloon.

In some embodiments, the catheter further comprises a light concentrator at a distal end of said tip section.

In some embodiments, the catheter further comprises a second wall, wherein said plurality of optical fibers are located between said first and said second walls.

In some embodiments, the catheter further comprises one or more imaging elements configured to provide information on an inner part of said blood vessel.

In some embodiments, the catheter further comprises one or more imaging elements for monitoring the procedure.

In some embodiments, the catheter further comprises one or more imaging elements configured to provide information on an inner part of said blood vessel.

In some embodiments, the catheter further comprises one or more lead retraction elements.

In some embodiments, the catheter further comprises one or more openings for administering a drug.

In some embodiments, the circumferentially-directed laser optics comprises a plurality of optical fibers located along an inner surface of a cylindrical tip section of the catheter.

In some embodiments, the device further comprises a light concentrator at a distal end of said tip section.

In some embodiments, the device further comprises one or more imaging elements configured to provide information on an inner part of said cavity.

In some embodiments, the device further comprises one or more openings for administering a drug.

In some embodiments, the device further comprises openings or tubing for flushing a cleaning solution.

In some embodiments, the device is configured for use in the gastrointestinal tract, urology or gynecology.

In some embodiments, the device is configured to mount on a tip section of an endoscope.

In some embodiments, the method further comprises administering a drug for preventing or treating restenosis.

In some embodiments, the method further comprises flushing a cleaning solution.

In some embodiments, the method further comprises imaging the inner part of said cavity.

In some embodiments, the method further comprises imaging the procedure.

In some embodiments, the method is used in endoluminal procedures in the gastrointestinal tract, urology or gynecology.

In some embodiments, the undesired tissue comprises a flat lesion and wherein the gastrointestinal tract cavity comprises an inner wall of the stomach.

In some embodiments, the undesired tissue comprises a flat lesion and wherein the gastrointestinal tract cavity comprises an inner wall surface of the stomach.

In some embodiments, the undesired tissue comprises a sessile polyp, flat polyps and NP-CRN (Nonpolypoid colorectal neoplasms) and wherein the gastrointestinal tract cavity comprises an inner wall surface of the colon.

In some embodiments, the undesired tissue comprises Barrett's tissue and wherein the gastrointestinal tract cavity comprises the esophagus, wherein said tip section is configured to match the typical anatomy of the esophagus.

In some embodiments, the undesired tissue comprises Barrett's tissue and wherein the gastrointestinal tract cavity comprises the esophagus.

In some embodiments, transmitting laser radiation and cutting are conducted simultaneously.

In some embodiments, transmitting laser radiation and cutting are conducted intermittently.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 1A shows an exemplary cylindrical tip section of a hybrid catheter in perspective view;

FIG. 1B shows an exemplary cylindrical tip section of a hybrid catheter in a front view;

FIG. 1C shows an exemplary cylindrical tip section of a hybrid catheter inside a vessel with partial plaque blockage in a cross-sectional view;

FIG. 3A shows a tip section which includes a hollow reflective light concentrator;

FIG. 3B shows a tip section which includes a solid-state light concentrating waveguide;

FIGS. 6A-B illustrate a tube 600 introduced through the catheter and ending with an array of nozzles or apertures FIGS. 7A-B illustrate the use of a roller 700 to stain the tissue FIGS. 8A-B illustrate apertures 800 built into the catheter's housing FIGS. 9A-B illustrate an array of tubes or needles 900a-b which are used to administer the drug

DETAILED DESCRIPTION

Figure 2:
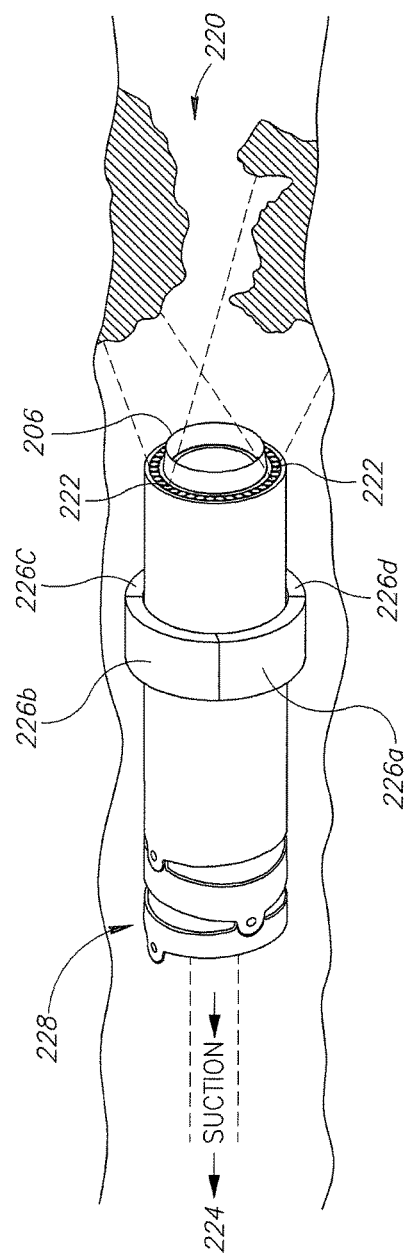
FIG. 2 shows an exemplary tip section of a hybrid catheter, with one or more alterations with respect to FIGS. 1A-C.

An aspect of some embodiments relates to a hybrid catheter and methods for using the same in endoluminal interventions. For example, present embodiments may be useful in various vascular applications, such as atherectomy, angioplasty, debulking of plaque in in-stent restenosis, leads extraction, thrombectomy in chronic peripheral and coronary artery diseases and for management of acute blockage of vessels in coronary and neurovascular applications. Another example is the use of embodiments in gastroenterology, such as for removal of sessile and flat lesions in the GI track, Barrett's Esophagus management and in analogous applications requiring removal of tissue from the inner walls in gynecology and urology interventions.

The hybrid catheter may be based on a combination of laser and mechanical removal (also "debulking") of an undesired material from a bodily lumen. In vascular interventions, the catheter may be configured to weaken and/or even cut and detach undesired material with a laser and then, even in cases where the plaque material was not entirely removed, detaching the rest of the plaque material by mechanical means, such as using a blade. The laser may change the mechanical characteristics of tissue, and thereby improve performance of mechanical tools such as various types of blades or shavers. By way of example, the laser may make a soft tissue crispier so it can be effectively crushed using the mechanical tool.

Advantageously, usage of the present catheter may obviate the need to photo-ablate (evaporate) most or all of the undesired material. Accordingly, the process may be faster and result in lesser by-products than in common laser ablation, lesser associated mechanical stress and lesser other side effects such as thermal injury resulting from photo ablation. The process may allow using smaller lasers wherein energy is focused at a smaller area and wherein mechanical tools remove traces remaining in the treated area and facilitate further penetration of the laser beam to proceed in effective ablation. In addition, challenging calcified tissue may be successfully treated, despite the difficulty in many of today's common mechanical or excimer lasers to delicately detach such tissue from the vessel's walls. The present catheter, advantageously, provides for controlled cutting of plaque with minimal or no damage to the vessel's walls.

This hybrid catheter disclosed herein may be used (for example in atherectomy) alone and/or in conjunction with low pressure balloon angioplasty, stenting, for treating in-stent restenosis with no damage to the stent, and/or for treatment of acute blockages due to plaques and or thrombus (thrombectomy).

The terms "cut", "dissect", "resect", "detach", "debulk" and "remove" may be used here interchangeably.

According to some embodiments, the catheter comprises a tip section, which may be essentially in a cylindrical shape, having circumferentially-directed laser optics, optionally in the form of one or more optical fibers, configured to deliver laser radiation, and a circular-action cutter including one or more blades configured to assist in cutting and/or detaching undesired materials (also "deposits") from an inner surface of a blood vessel. The one or more optical fibers may be circumferentially-directed, namely, they may be located along an inner surface of the cylindrical tip section, which is near the periphery of the tip section. Alternatively, the circumferentially-directed optical fibers may be located elsewhere but directed, by way of orientation and/or optical focusing, to radiate an area in front of the circumference of the tip section.

The circular-action cutter may be located in a central part of the tip section, for example, surrounded by the optical fibers. Alternatively, the circular-action cutter may be located in the periphery of the tip section and the one or more optical fibers are located in a central part of the tip section, for example, surrounded by blades.

According to some embodiments, the one or more optical fibers and the one or more blades are located in the periphery of the tip section.

According to some embodiments, the one or more optical fibers and the one or more blades are located in a central part of the tip section.

According to some embodiments, the circular-action cutter lays on a spring so that a maximum force applied by the cutter is predetermined in order to avoid potential damage, yet be effective. The tip section may include an inner channel maintained at a relative low pressure to suck the undesired material which may be plaque, thrombus material, debris, saline solution used for cleaning and/or the like.

Optionally, a motor is provided to rotate the circular-action cutter in order to improve fragment cutting and/or detaching. Additionally or alternatively, the motor or a different motor may be used to rapidly vibrate the circular-action cutter in order to improve fragment cutting and/or detaching.

Optionally, the circular-action cutter is heated to improve its performance. This may be done by an external heat source, electrical means and/or by the laser radiation.

According to some embodiments, the catheter tip may be expandable, such that its diameter may be increased after its introduction into the vessel.

According to some embodiments, the catheter tip may include means for deflection, such that effective working area will be larger than the catheter diameter and enable off-axis work.

According to some embodiments, the catheter may be useful in cases of Chronic Total Occlusions (CTO), where a guidewire cannot normally be used to pass lesions totally blocking the vessel, and therefore atherectomy is often not feasible, since usage of a guidewire often dictates a certain relative position, and angle in particular, of the catheter's tip section versus the vessel.

An example of an appropriate laser of some embodiments is a solid state ultraviolet (UV) laser emitting pulses in approximately 355 nm and/or 266 nm. An example of an appropriate laser is the Qauntel CFR400, emitting 50 mJ, 10 ns pulses of 355 nm at 50 Hz and/or 40 mJ of 266 nm at 40 Hz. Another example is an Excimer laser.

In case of using significantly high repetition rates, thermal effects in the tissue may become a problem. This can be at least partially resolved by minimizing ablation area (depth and width), use of short laser pulses and with saline flushing. Another option includes sequential illumination of fibers in a manner that not all the fibers are exposed to laser ration simultaneously, in order to enable thermal relaxation of the affected tissue.

In an embodiment, dyes or substrates may be used to enhance absorption at certain wavelengths, such as 355 nm. For example, sensitization with haematoporphrin or tetracycline prior to the procedure, in order to enhance ablation of the pretreated atheromatous plaque but not insensitised or normal arterial wall.

Another example of a laser of some embodiments is a laser emitting pulsed radiation in the mid-infrared (IR) region, such as in the range of 2.8-3 micrometers, a range where water is very effectively absorbed. Additionally or alternatively, radiation at around 2 microns may be used, with a preference for thulium laser emitting at 1910-1940 nm range wherein there is higher absorption of water preferably combined with Q-switched modulation wherein ablation is more effective and reduces lateral damage. For 3 micron emission, an Er:YAG may be used, or another source such as a Mid-IR Holmium Fiber Laser Directly Pumped with Diode Laser that emits at 2840 nm using fluoride fibers [see *Optics Letters*, Sep. 1, 2007, pp. 2496-2498].

Yet another example is usage of a third harmonic of a Nd:YAG laser at 355 nm, preferably a compact, all solid state, diode pumped laser. The 355 nm radiation usually has a deeper penetration capability compared to the 308 nm radiation, in the depth range of 100 micron or more in relevant tissues and materials. Optionally, very short pulse widths (such as <10 ns) are used, in order to obtain a higher power density, and, in particular, to be able to ablate calcified plaques. In accordance with some embodiments, the energy per pulse is in the range of 10-100 mJ and the pulse frequency is in the range of 10-100 Hz. Optionally, the area of ablation may be flushed with a saline solution in order to reduce side effects (such as cavitation), clean the area of ablation and catheter and/or facilitate collection of debris.

One of the advantages of using 355 nm radiation is that is considered relatively nonmutagenic. The 308 nm radiation of the xenon chloride laser is in the UVB range, which is known to have mutagenic risks. [Walter Alexander. Journal of Clinical Laser Medicine & Surgery. AUGUST 1991, 9(4): 238-241. doi: 10.1089/clm.1991.9.238.]

Some prior studies have indicated that third harmonic lasers are generally less suitable to endovascular interventions than 308 nm lasers, due to longer penetration rates and reduced effectiveness of ablation (see, for example, Grundfest WS et al., Am J. Surg. 1985 August; 150(2):220-6; and Frank Laidback et al., Lasers in Surgery and Medicine 8:60-65 (1988)). The present embodiments, however, may successfully utilize third harmonic Nd:YAG lasers instead of complex and expensive Excimer lasers. The present embodiments address several problems. For example, in some embodiments, it may not be necessary to laser-ablate all the material whose removal is desired, but rather the laser and the mechanical cutter may share the task; the laser may ablate and/or weaken at least some of the material, while the mechanical cutter completes the job by finally detaching the material from the walls.

In some embodiments, a laser that emits radiation in 266 nm may be used. This wavelength has a shorter penetration rate in addition use of compact Excimer laser emitting radiation at 308 nm, as currently used, can be utilized with the current embodiments. According to some embodiments, a system may include means that enable an operator to switch between 266 nm and 355 nm, generated from the same Nd:YAG laser, and means to control power, repetition rate and/or exposure/illumination of specific fiber groups.

An alternative embodiment of the present invention replaces UV lasers with a laser with radiation in the 2 micron or 2.8-3 microns, in which ablation is very effective.

Holmium lasers are conventionally used for 2 microns but Thulium lasers have a stronger water absorption and smaller absorption length, which makes them especially suitable for some embodiments. For example, in an embodiment, pulsed fiber thulium laser is used. Alternatively, a solid state laser may be used in order to increase pulse power per pulse, which is currently limited in fiber lasers and in view of the limited pulse rate that can be used in order to minimize heat accumulation and damage.

Laser in 2.8-3 micrometer may be Er:YAG. Er:YAG Q-switched are available with pulses in the hundreds of nanosecond range, which may be suitable for present embodiments. See, for example, M. Skorczakowski, et al, Laser Physics Letters Volume 7, Issue 7, pages 498-504, July 2010. Another laser example which may be suitable for specific embodiments is Pantec's model DPM-15 solid state laser, emitting microsecond pulses in the mJ range at hundred of KHz.

In an embodiment, fiber lasers which may be directly diode-pumped, such as a Mid-IR Holmium Fiber Laser, are used. This laser may be pumped from ground level ($^5I_8$) to an excited energy band ($^5I_6$) with radiation at about 1150 nm, and the relaxation bands may lead to emission at 2840 nm (relaxation to band $^5I_7$) and 2100 nm in relaxation to ground state. Accordingly, this laser may be directly pumped with recently developed high-power, high-brightness diode lasers based on highly strained InGaAs quantum wells that produce output at 1148 nm. See Optics Letters, Sep. 1, 2007, pp. 2496-2498 and Stuart D. Jackson Optics Letters, Vol. 34, Issue 15, pp. 2327-2329 (2009).

The laser may be selected according to the selected resonator optics, for example fluoride fiber lasers to emit laser radiation on the 2.9-μm transition (516 to 517) and silica fiber lasers to emit radiation on the 2.1-μm transitions (517 to 518). An advantage of an embodiment using a laser in the region of 2.9-3 micron is that the absorption is very high and results in very short length of absorption, in the order of 15 microns only. Therefore, the relaxation time is shorter so the pulse rate may be increased to above 100 Hz in order to accelerate the procedure.

In addition to the laser beam that interacts with the undesired material, a laser with controlled pulse rate and/or power may be used to interact with the liquid between the fiber tip (exit of laser beam) and tissue, either to allow for "opening" of a passage for the beam (e.g., a channel wherein light is not absorbed when UV radiation is used) to the tissue prior and adjunctive to the required interaction with the tissue, and/or to facilitate the process (when mid-IR radiation is used) benefiting from the "water spray" effect. By way of clarification the tip can be in mechanical contact with the tissue being ablated or not.

Reference is now made to FIGS. 1A, 1B and 1C, which show an exemplary cylindrical tip section 100 of a hybrid catheter in perspective, front and cross-section views, respectively, in accordance with an exemplary embodiment. The remainder of the catheter's shaft (not shown) may, in some embodiments, be biocompatible polymer tubing, optionally coated, to minimize friction with the vessel's walls.

Tip section 100 is positioned at the distal end of the hybrid catheter, the end which is inserted into the blood vessel. Tip section 100 may include a housing 102, for example a cylindrical one, at least one optic fiber(s) 104 positioned along an inner surface of housing 102, and a circular-action cutter (or simply "cutter") 106 positioned inwardly of the optic fibers. Alternatively, in an embodiment (not shown), the circular-action cutter may be positioned outwardly of the optic fibers. It is intended that the following description of the embodiments in which the circular-action cutter is positioned inwardly, be applied, mutatis mutandis, to the alternative, not-shown embodiment. Optionally, optic fiber(s) 104 are delimited and/or supported by a first inner wall 108. Further optionally, cutter 106 is delimited and/or supported by a second inner wall 110.

In accordance with some embodiments, the catheter is used with a standard guidewire.

In accordance with some embodiments, the catheter is connected to a suction pump that generates low pressure to collect undesired material, saline and/or the like through the catheter. The pump may be a peristaltic pump, which mounts externally to the fluid path, to avoid any contamination of the pump. Optionally, this obviates the need to use disposable parts.

Optic fibers 104, serving as the laser optics of the present hybrid catheter, may be connected, at their proximal end (not shown) to a laser source characterized by one or more of the parameters laid out above. Optic fibers 104 may deliver the laser beams from the source towards the intervention site in the body. In tip section 100 of FIG. 1C, optic fibers 104 are shown as they emit laser towards undesired material 114. One or more areas 116 in undesired material 114 may consequently be modified or even ablated by the laser. Then, cutter 106 may more readily cut into undesired material 114 and detach at least a part of it from the vessel's walls 118.

Cutter 106 is optionally an annular blade extending to a certain depth inside tip section 100 and coupled to a suitable motor (not shown), located in the tip section or further in the shaft, supplying rotary and/or vibratory power to the blade. Optionally, one or more flexible members, such as a spring 112, may interact with cutter 106 at its base, to allow it to retract and protrude from housing 102. Tip section 100 of FIGS. 1A-C is shown with cutter 106 in its protruding position, while tip section 100b of FIG. 1C is shown with the cutter, now marked 106b, in its retracted position. The length of protrusion out of housing 102 may be, for example, up to about 350 microns when treating blood vessels. When protruding, cutter 106 is used for detaching undesired material (also "deposit") 114 from an inner surface 118 of a blood vessel 120. According to some embodiments, when a certain force (for example, above a predetermined value) is applied to cutter 106 from the front, which may be a result of blockage in blood vessel 120, the cutter may shift its position and retract into housing 102.

The annular blade of cutter 106 may have sufficiently thin edges, such as around 100 microns. Suitable blades may be tailor-made by companies such as MDC Doctor Blades, Crescent and UKAM. The blade may optionally be mounted at the end of a rotatable tube rotated. Such tubes are available from manufacturers such as Pilling, offering a line of laser instrumentation and blade manufacture. The blade may be metal or manufactured by molding a material such as plastic which is optionally coated with a coating having proper characteristics for in-vivo use.

An exemplary tip section may have an external diameter of approximately 5 mm, an internal diameter (within the innermost layer, be it the cutter or an extra wall) of approximately 3.4 mm, and optical fibers each having an approximately 0.1-0.2 mm diameter.

Reference is now made to FIG. 2, which shows an exemplary tip section 200 of a hybrid catheter, which may be similar to tip section 100 of FIG. 1 with one or more alterations: First, one or more fibers 222 of the optical fibers existing in tip section 200 may be used for imaging the lumen of a blood vessel 220 by transporting reflected and scattered light from inside the lumen to an external viewing and/or analysis device (not shown) located externally to the body. This may aid in avoiding perforation of vessel 220 and allowing for on-line monitoring of the intervention process. Second, tip section 200 may be maneuverable, so as to allow different viewing angles and/or in order to align the laser beams and a cutter 206 differently. Third, a cleaning channel (not shown) may be present inside tip section 200 and extending outside the body, through which channel suction 224 is applied in order to evacuate debris of the undesired material which were treated by the lasers and/or cutter 206. These optional alternations are now discussed in greater detail:

A conventional manner for detection of plaque and other lesions and for monitoring of vessel treatment is based on ultrasound and fluoroscopy. Here, however, one or more fibers 222 may be utilized for detection of lesions and/or to monitor the intervention process on-line, based on the reflection and/or scattering of the laser light from the vessel and/or the deposits. Alternatively or additionally, a different source of illumination may be used, such as through one or more other fibers. The captured light may be transmitted to a sensor such as a CCD, a CMOS or a MOS. The sensing may include a filter or means for spectral imaging, to gain information about the material characteristics (plaque, tissue, calcified plaque, blood clot, etc.). This may enable a quick and effective procedure with minimal risk of perforation, and may enable debulking procedures wherein a guidewire cannot or should not be used.

The angle of tip section 200 may be controlled to enable by means of tip deflection material removal in a cross-section larger than the catheter size. This may be done by mechanical means, such as by selective inflation and deflation of at least two balloons (not shown) attached to the tip section externally at different angles, or a balloon with different compartments 226a-d. Another example is usage of links forming a joint 228, controllable from outside the body using one or more wires (not shown).

The laser optics of some embodiments will now be discussed in greater detail. The laser beam may be directed through fibers each having a core diameter optionally in the range of 40-250 microns. In a configuration where the catheter's circumference is, for example, 15 mm, using fibers with an outer diameter of 50 microns will result in using approximately 300 fibers with a cross-section area smaller than 1 mm$^2$, so that for a coupling efficiency of 75%, the energy at the exit of each fiber will be close to 40 mj/mm when pumped with a 50 mJ laser. Adequate fibers for some embodiments may be all-silica fibers with a pure silica core. These fibers can usually withstand about 5 J/cm$^2$ in the input. Some embodiments include fibers with a numerical aperture (NA) in the range of 0.12-0.22. An example of a relevant fiber is FiberTech Optica's SUV100/110AN fiber for UV application and the low OH version SIR100/140AN for use with laser in the 1900-2100 nm range or Infrared Fiber Systems, IR Photonics and A.R.T. Photonics GmbH fibers for transmission of radiation in the 2900-3000 range. Embodiments of single mode or multimode may be realized while preservation of beam quality is important but not mandatory in certain embodiments. Some embodiments may include microlenses at the tip area to manipulate the beam at each individual fiber exit.

The power required for effective ablation with 355 nm, 10 nsec pulses (approximately 30-60 mJj/mm$^2$) is close to the damage threshold of certain fibers or above it, which lead, in existing products, to the need of extended pulse length, for example. According to some embodiments, high peak power is maintained and accordingly the catheter may include means for delivery of the laser power through relatively bigger optical fibers, e.g. 100 or even 300 micron fibers that do not extend all the way to the end of the tip section, as schematically illustrated in FIGS. 3A-3E.

FIG. 3A shows a tip section 300 which includes a hollow reflective light concentrator 304a with a straight profile or a concave profile (as shown), used to concentrate light from at least two fibers (shown jointly at 304). Hollow concentrator 406a may have metal-based or dielectric coating. Hollow concentrator 304a may form a ring shape surrounding a cutter 306, in manner that radiation from all the fibers is delivered with one concentrator, so that a relatively uniform ring of pulsed radiation is generated at the exit. The exit may include a window (not shown in the figure). Optionally, the optical path may be maintained clean with flushing of saline. Flushing may be through an opening in the front or from the side, between the catheter and an extra lumen that can also facilitate catheter movement in the vessel or in certain embodiments through the central lumen.

FIG. 3B shows a tip section 330 which includes a solid-state light concentrating waveguide 334a for concentrating light from at least two fibers (shown jointly at 304). Solid-state waveguide 334a may be made, for example, of Silica with a reflective coating, or a combination of two materials such as Silica and Fluoride-doped Silica.

Solid-state waveguide 334a may be optically coated at the interface with the fiber(s), to improve optical throughput from the fiber(s) to the concentrator. Alternatively, the two may be welded.

Figure 3D:
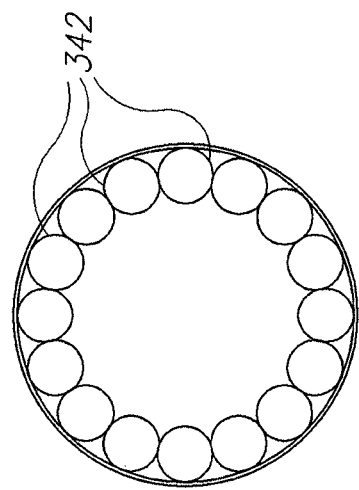
FIGS. 3C-3E show the usage of tapered fibers.
Figure 3C:
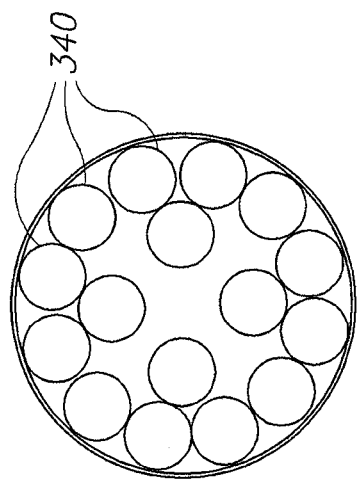
Figure 3E:
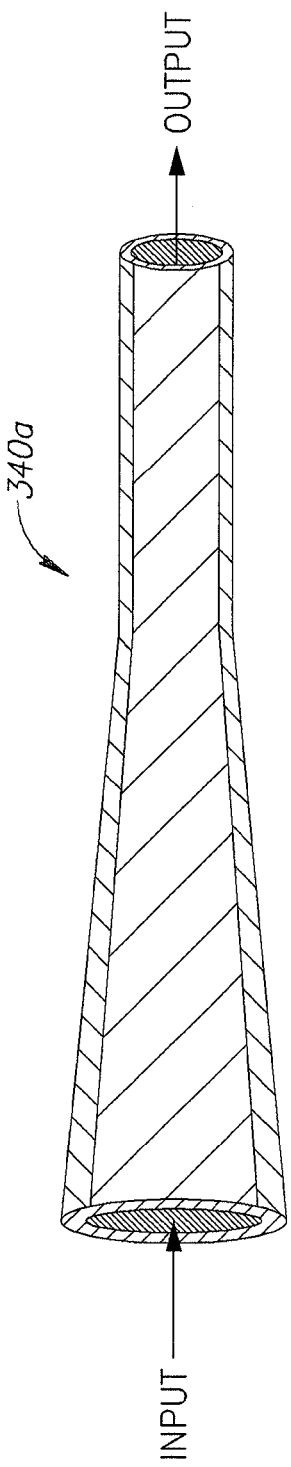

FIGS. 3C-3E illustrate the usage of tapered fibers, such as those available from Oxford Electronics. The fibers may be thick 340 at the proximal end of the catheter's shaft, and thin 342 at its distal end—as seen in cross-section. FIG. 3E shows a single tapered fiber 340a in perspective view.

Figures 4A, 4B:
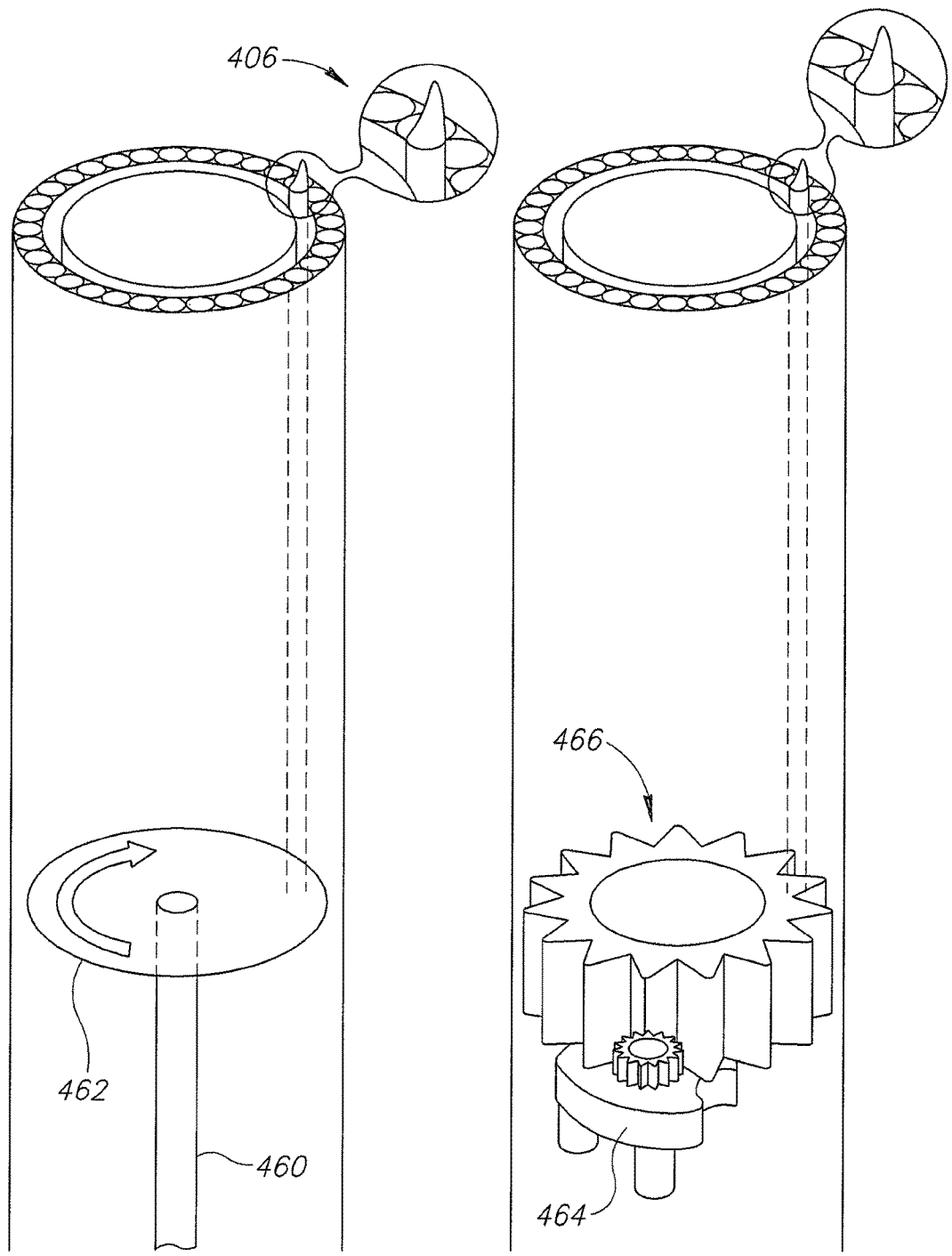
FIGS. 4A-4B show a circular-action cutter.

Reference is now made to FIG. 4A, which shows another option for a circular-action cutter, in accordance with an embodiment. The circular-action cutter here may be a rotating blade 406 which is rotatable, for example, using a flexible shaft 460 which centrally rotates a plate 462 peripherally connected to the rotating blade. Flexible shaft 460 may be capable of delivering a limited amount of torque, especially when there is bending in the artery, etc. Common mechanical atherectomy devices sometimes use very high rotation speeds to compensate for that. Present embodiments reduce the need for high moments, as the blade is active in an area which has been prepared, namely—cut or at least modified by the laser. Furthermore, the fact that lower torque and rotating forces are applied to the atheroma/plaques, decreases the radial forces applied to the vessels.

Reference is now made to FIG. 4B, which is mostly similar to FIG. 4A, except for the way rotating blade 406 is being rotated. Rotating blade 406 may be rotated by a miniature motor 464 and suitable transmission 466. Appropriate miniature motors are available from manufacturers such as Namiki, which developed a 1.5 mm-diameter micro-geared DC motor.

Optionally, rotating blade 406 of FIGS. 4A-4B may have shapes that facilitates collection and/or scraping of debulked material, to facilitate collection of debris.

Figure 5:
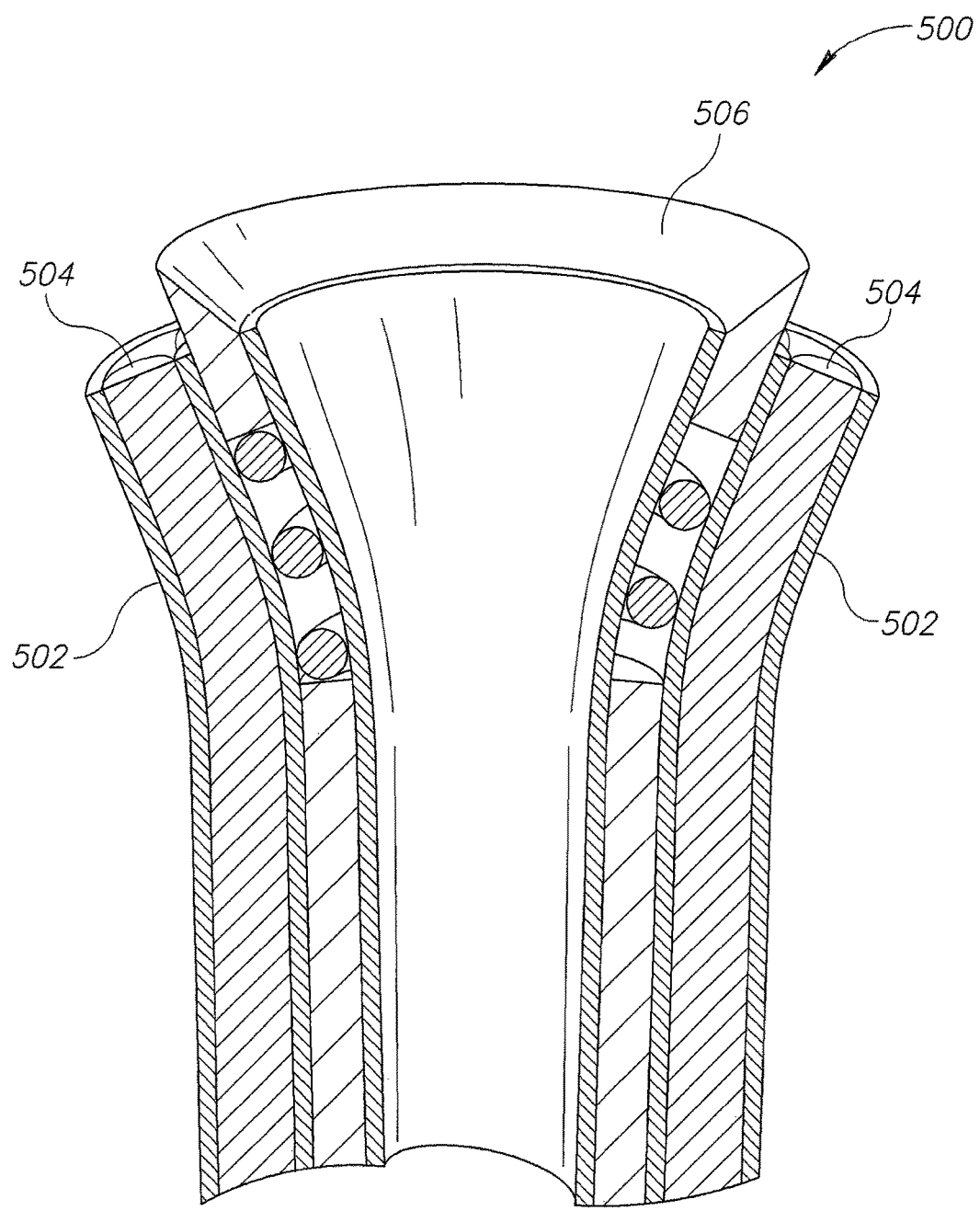
FIG. 5 shows a cross-sectional view of an expandable tip section.

In order to enable effective debulking in blood vessels, catheters of different dimensions may be used, for example in the range of 4-22 French (approximately 1.3-7 mm). The use of a larger catheter holds the advantage of enhancing the intervention process, but raises an issue of a large opening required for introduction into the vessel and/or accessibility within the vessel itself. Therefore, according to some embodiments, the diameter of the catheter, at least at its tip section, may be expandable. A first example is shown in FIG. 5, which is a cross-sectional view of an expandable tip section 500. A housing 502 of tip section 500 may be made of a relatively flexible material, compared to the rest the catheter's shaft. When the catheter reaches the debulking site, tip section 500 is expanded, to form an outwardly-tapered shape. This expansion may be achieved by introducing a mechanical element which applies pressure on one or more parts in tip section 500. Fibers 504 that transmit the laser beam, may then be inserted into the catheter's walls. Since when the tip section 500 is expended the distance between the fibers also extends, more fibers may be inserted into the walls. Optionally, the mechanical element introduced to expand tip section 500 includes cutter 506. Optionally, expandable tip section 500 may be used in conjunction with the tip section deflecting means of FIG. 2.

In another embodiment of a catheter with an expandable tip section, materials with shape memory, such as Nickel Titanium (known as Nitinol), may be used. The catheter, or at least its tip section, is compressed before introduction into the body, and naturally returns to its pre-compressed shape after it is introduced to the lumen. Nitinol may be used in a structure of a mesh or a braid, to provide sufficient radial force while enabling contraction with low enough radial forces when the catheter is retracted. Some flexibility may still remain at the tip section, to allow accommodation to the physiological shape of lumen. The tip may also include means for controlled deflection.

In some embodiments, the catheter may perform local delivery of drugs which reduce the incident of restenosis, such as Paclitaxel and its derivatives, or soluble forms such as Coroxane. The drug may remain in the site post-treatment and assist in lumen recovery, while preventing overdosing and systematic effects.

The drug administration following the removal of undesired material from the vessel or stent may be achieved by means such as: (i) spraying of drug from nozzles in the external surface of the catheter, or with a tube that includes an array of nozzles at its end, threaded through a suitable channel in the catheter; (ii) by a roller that "paints" the tissue; (iii) by a drug-coated balloon; (iv) by a balloon that includes means to deliver drug through channels in its wall; (v) brushes in the catheter walls; (vi) tubes with nozzles which may change their direction on the way in and out the material removal site.

To optimize long-term efficacy, some embodiments provide means for deep administration of the drug, to be sustained in the deeper layers of the arterial wall or even in remaining plaque but not in the endothelium, thereby allowing new endothelial cells to grow and re-align the lumen, to inhibit restenosis in deep cell layers after the lumen has been restored and re-endothelialized. This may be accomplished by means such as pressure-controlled drug administration, administration below the surface and/or selection of adequate drug forms.

In order to increase absorption of plaque material, the treatment procedure may include administration of one or more substances that increase absorption of plaque at 335 nm such as treating with tetracycline for which the uptake by plaque is a few times larger than in normal tissue. See, for example, Murphy-Chutorian D, et al, Am J. Cardiol. 1985 May 1; 55(11):1293-7.

For blood vessel treatment, it is often desired to administer the drug in the deeper layers of the arterial wall but not in the endothelium, thereby allowing new endothelial cells to grow and re-line the lumen. As a result, the drug continues to inhibit restenosis in deep cell layers after the lumen has been restored and re-endothelialized, while, on the other hand, overdosing and systematic effects are eliminated. In some of the cases some plaque material remains on the vessel's walls or stent and the drug formulation and means of administration should take it in account.

Examples of applicable drugs include: Elutax®, SeQuent®, Cotavance™ with Paccocath® coating technology, TADD (from Caliber Therapeutics, Inc.), Advance® 18PTX®, DIOR®, IN.PACT™ Amphirion, Coroxane and more.

The conventional way to administer these drugs to avoid restenosis is with coated balloons. Alternative drug forms such as Coroxane may be administered via IV promptly after the procedure, but this would not result in local administration. It has been suggested in the literature to perform a two step process wherein a coated balloon follows atherectomy, but this would result in a more complex and costly procedure that can limit routine clinical use.

FIGS. 6A-B, 7A-B, 8A-B and 9A-B include schematical illustrations of a number of exemplary tip section embodiments suitable for local administration of drugs.

FIGS. 6A-B illustrate a tube 600 introduced through the catheter and ending with an array of nozzles or apertures 602 that spray the drug on demand.

FIGS. 7A-B illustrate the use of a roller 700 to stain the tissue. The catheter may include means to allow the roller to get at least partially inside a groove 702 before the debulking procedure, and exit the groove when needed to transfer the drug to the tissue. Roller 700 may include means to apply pressure to the walls in order to increase drug delivery and/or expand the stent in in-stent restenosis (ISR) applications.

FIGS. 8A-B illustrate apertures 800 built into the catheter's housing, and configured to be opened only when needed.

FIGS. 9A-B illustrate an array of tubes or needles 900a-b which are used to administer the drug in a manner that will increase its sustainability. Means to allow the angle of the tubes relative to the catheter to change before and after the debulking procedure and/or in the way inside and outside from the lumen/stent are provided. The tubes may be facing forward 900a when moving forward and backwards 900b when moving backwards. The tubes are optionally made of a flexible, biocompatible material.

Further examples of drug administration may include: a brush to transfer the drug through nipples in the wall of the catheter; a balloon for administration of drug; a balloon surrounding the catheter and being coated with the drug and inflated after the debulking procedure; a balloon with nipples that are used to administer drug on demand; and a coated balloon inserted through the cleaning channel of the catheter.

The embodiments disclosed herein are brought as examples and can be combined for the purpose of vascular intervention in peripheral, coronary and neurovascular applications in chronic and acute conditions and in other medical applications wherein stents have to clean such as in gastro and urology and in applications wherein lumens have to be created or extended such as Benign Prostatic Hyperplasia.

Another clinical application, according to some embodiments of the present invention, is in removal of undesired tissue from a body cavity during an endoluminal procedure. Such procedures can be performed for example in gynecology, urology and in gastroenterology.

Figure 10:
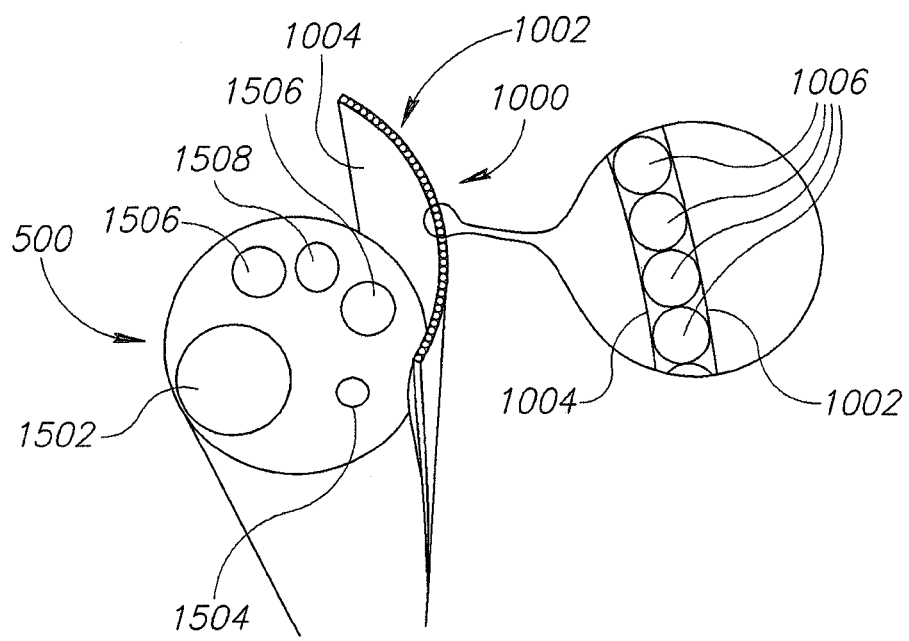
FIG. 10 shows an exemplary tip section of a hybrid device mounted on an endoscope.
Figure 11:
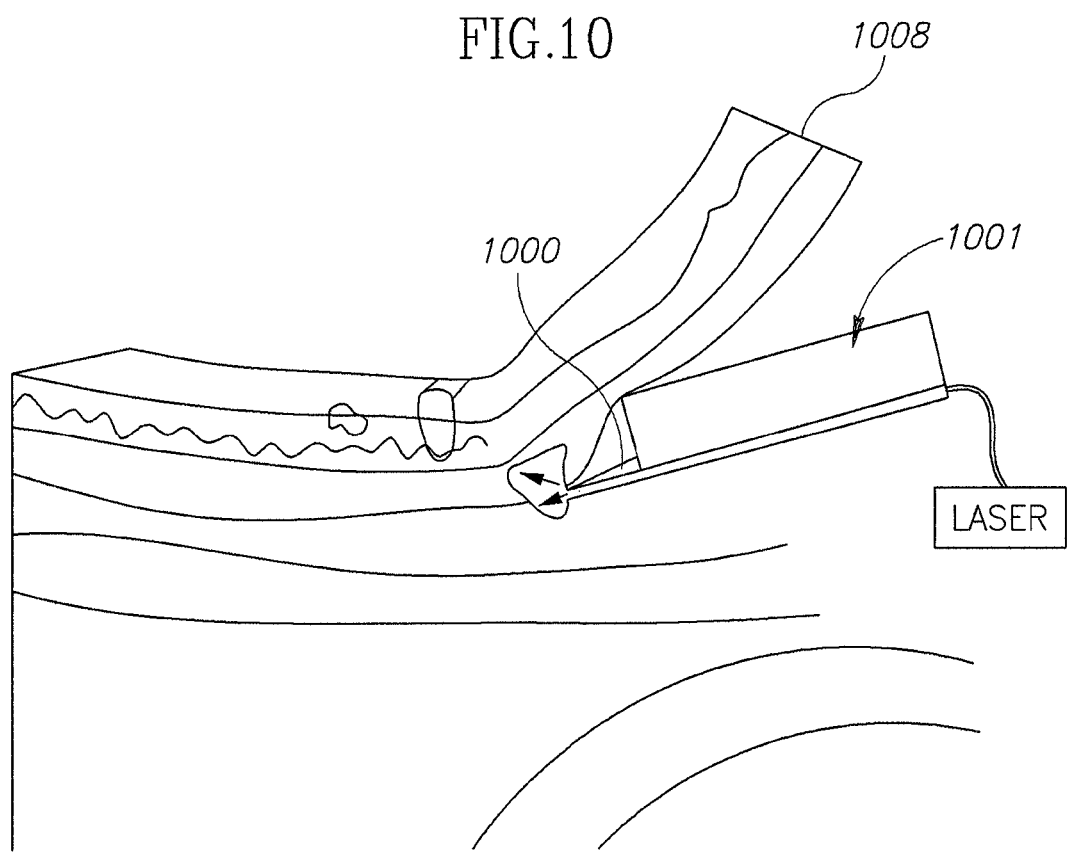
FIG. 11 shows a hybrid catheter mounted on an endoscope, during a procedure of detaching undesired tissue.
Figure 12:
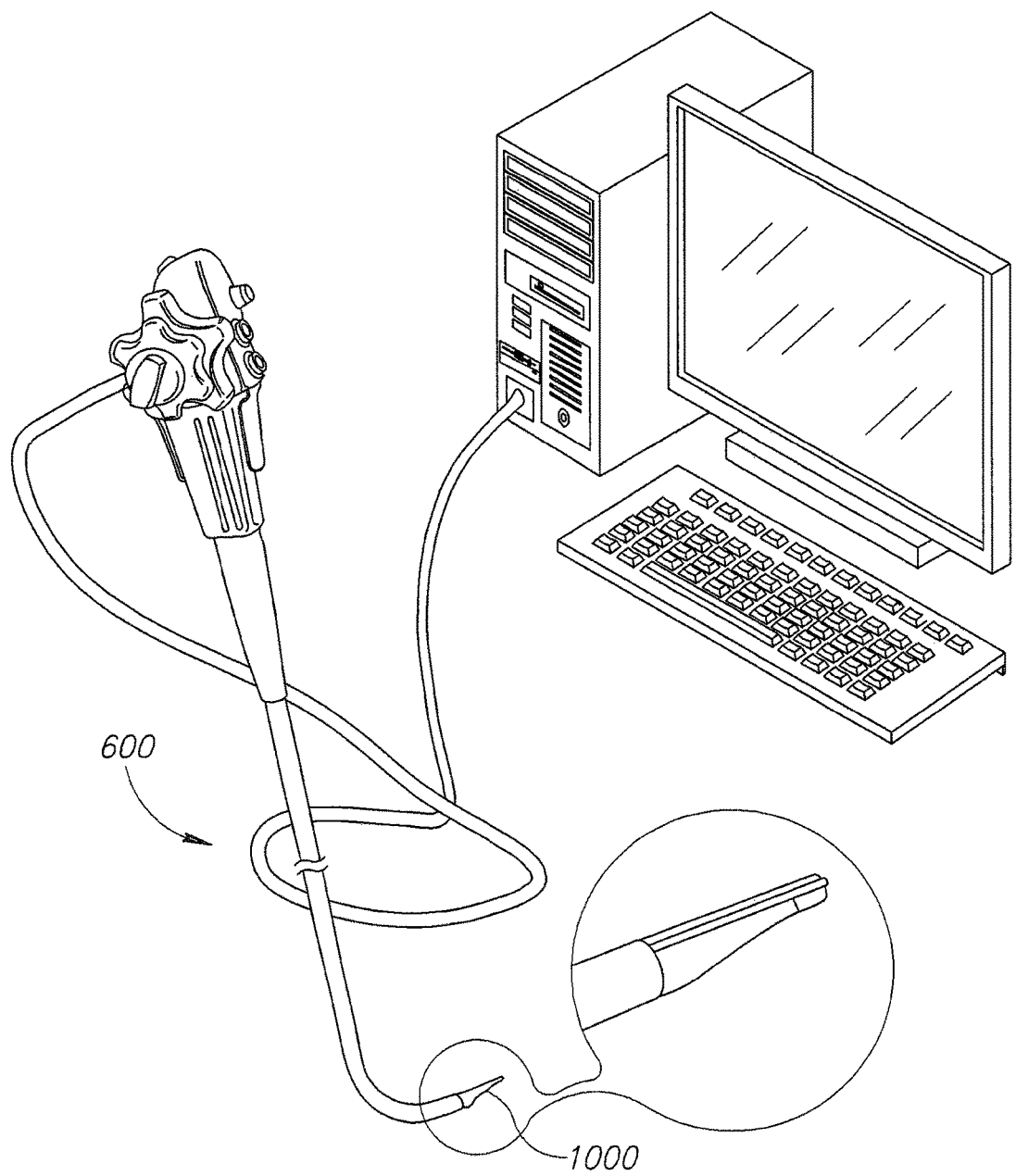
FIG. 12 shows a catheter assembled on a commercially-available endoscope.

Such procedures may include, for example, removal of flat and/or large lesions in the gastrointestinal (GI) track and in management of Barrett's esophagus. The motivation is to remove the undesired pathological tissue with minimal complications (e.g., in case of Barrett's esophagus, without esophageal perforations and strictures). This clinical application may require modified embodiments of the hybrid catheters disclosed herein in accordance with some embodiments. FIG. 10-FIG. 12 illustrate catheters for detaching undesired tissue from an inner wall of a body cavity, for example, but not limited to, Barrett's esophagus management, according to embodiments of the invention.

The first embodiment is a hybrid catheter which combines a utility of laser radiation to ablate and cut/detach the undesired pathological tissue or modify its mechanical characteristics and mechanical means such a blade or a sharp edge of a wall of the catheter to complete the detaching. This way, the tissue is resected/disected using the laser radiation and the blade/wall's edge. Thus the blade/wall's edge does not need to be too sharp and are thus configured to cut the tissue without the risk of potential perforation or damage to the body cavity.

Reference is now made to FIG. 10, which shows an exemplary tip section 1000 of a hybrid device in perspective view, mounted on an endoscope 1500, in accordance with an exemplary embodiment. The remainder of the catheter namely—its shaft (not shown) may, in some embodiments, be biocompatible housing, optionally coated so as to reduce friction with the cavity's wall. Endoscope 1500 may be any commercially available scope having, inter alia, working channel 1502, for insertion of medical tools, water/air injector(s) 1504 for cleaning and insufflation, and illuminators 1506. Endoscope 1500 may also include a camera 1508 including CCD, CMOS or MOS sensors for example and optics.

Tip section 1000 is positioned at the distal end of the hybrid catheter, the end which is inserted into the body cavity such as the esophagus. Tip section 1000 has a shape of a sector of a cylinder and is generally configured to be mounted on top of an endoscope (for example, as used in upper endoscopy or colonoscopy). The shape of tip section 1000 is also configured match the typical anatomy of the body cavity to which it is intended to be inserted. Of course, the tip section of the hybrid catheter (device) may have other appropriate shapes and forms, and can mounted in certain embodiments on another working tool that is used to manipulate it while the process is monitored with another camera such as in laparoscopic procedures. Tip section 1000 may include two walls, an external wall 1002 and an internal wall 1004. One of the walls (external wall 1002 and an internal wall 1004) or both of them may have sharp distal edges to facilitate cutting through the undesired tissue. One of the walls (external wall 1002 and an internal wall 1004) or both of them may be coated with a material that provides sharper edges. At least one optic fiber(s), typically a plurality of optical fiber(s) 1006 are positioned between external wall 1002 and an internal wall 1004. Alternatively, in an embodiment (not shown), there may exist only one wall and the optic fibers may be located along an internal or an external surface thereof. Alternatively, in an embodiment (not shown), there may exist a cutter (similar to the cutter shown in FIGS. 1A-C only having a shape of a sector of a cylinder). In another embodiment, external wall 1002, an internal wall 1004 and/or a cutter (blade) may have two positions, retracted position and protruded position (configured for cutting).

The external wall 1002, an internal wall 1004 and/or a cutter (blade) are configured (such as by virtue of sharpness) to cut through the undesired tissue and thereby detach at least a part of the undesired tissue from the inner wall of the body cavity. If a blade is present, it may be a rotary-action blade and/or a vibrating blade. According to some embodiments, optical fibers 1006 are configured to transmit laser radiation configured to modify an area of the undesired tissue thereby preparing said area for penetration of external wall 1002, an internal wall 1004 and/or a cutter (blade).

According to some embodiments, the blade may be mounted in a spring so that when force is applied beyond a certain predetermined level the blade enters into its compartment (shifts to retracted position). Alternatively, in another embodiment the position of the blade may be controlled by a physician. This way, the blade is not sharp enough to cut the tissue without the laser so as to avoid potential perforation. Flushing of saline or another appropriate solution at the edge of the catheter may be used to maintain an optical clean path, remove unnecessary material and reduce potential thermal damage and use a "water spray" effect with mid-IR radiation sources.

Reference is now made to FIG. 11, which shows a hybrid catheter mounted on an endoscope, during a procedure of detaching/resecting ("peeling") an undesired tissue, according to some embodiments. Hybrid catheter 1001 includes a tip section 1000, transmitting laser radiation and cutting through the tissue. In this figure, hybrid catheter 1001 is used to remove the Barrett's tissue 1008. The illustration shows that different layers can be targeted and removed. Barrett's tissue 1008 (or any other undesired tissue) is cut by catheter and lifted. The catheter, such as catheter 1001, may be (not necessarily) assembled on a commercially available endoscope, such as endoscope 1600 (FIG. 12). According to some embodiments, the tip section of the hybrid catheter (particularly but not limited to) in interventions in the GI track may be position in predetermined angle versus the scope axis and thereby predetermining the depth of penetration of the tip according to the peeling depth required.

"Peeling" like mode can be thought of in analogy to a "carpenter plane" but using a "hybrid blade". The depth of peeling can be adjusted according to the clinical condition such as the depth for Barrett's removal or required according to the stage of the disease and similarly in flat lesion in other places of the GI track. Accordingly the position of the blade knife can be adjusted as well as the distance between the blade and the plane. The catheter with a hybrid blade can be located at a predetermined angle/position and distance from the plane of the endoscope or another tool used to hold the tip. In this embodiment that catheter can be used to make the initial incision of the tissue as a few laser pulses are used to enable generation of a cut to allow the blade to cut through the required layers and then followed by movement of the catheter with the help of the scope over the organ in forward or backwards direction according to the position angle of the catheter.

In accordance with some embodiments the catheter is inserted through the working channel of a standard endoscope or through a special opening made in a dedicated scope. Some embodiments include using a tip with a memory shape that is contracted for introduction through the working channel and is expanded when it exits the endoscope tip. Such a catheter may be based on use of Nitinol. These embodiments enable the physician to perform a diagnostic procedure and, if a pathology is found, to introduce the resection catheter.

In another embodiment depending on the pathology the laser wavelength can be selected to enable reduced tissue penetration or surface ablation such as in 355 nm or 2.8-3 microns lasers or deeper with the 266 nm laser. For below the surface tissue interaction an embodiment of the invention includes a use of a mid-IR laser which had a longer penetration depth. A Thulium laser (potentially a Thulium fiber laser@lambda=1908-1940 nm, wherein wavelength is matched according to the embodiment to compensate for water absorption wavelength change depending on temperature) may be used for this application since it has a better matching with water absorption length around 2 microns compared to Holmium:YAG and accordingly penetration depth is limited to a few hundred microns and also pulse rate can be increased comparing to Holmium without thermal damage.

One of the potential advantages in using the "hybrid catheter" for debulking of required tissue from lumens such as in the GI track is the side effect of the laser and this is enhancing homeostasis and avoid bleeding. Depending on the specific laser used the effect may not be sufficient to avoid bleeding and some embodiments may include use of an additional laser for the purpose of hemostasis preferably delivered through the same optical fibers.

In accordance with some embodiments, the catheter is connected to a suction pump that generates low pressure to collect undesired material, saline and/or the like through the catheter. The pump may be a peristaltic pump, which mounts externally to the fluid path, to avoid any contamination of the pump. Optionally, this obviates the need to use disposable parts.

The hybrid catheter blade can also be used for improved biopsy procedures enabling relative large sample to be collected for further histology analysis and thereby decrease sampling errors, which are associated with high risk in patients with BE or in gynecology and urology applications.

According to some embodiments, the hybrid catheter may further include imaging means to detect the required area that has to be treated and to monitor the process on-line, thereby enabling effective "focal therapy" according to the diseases severity from early stage such as Barrett's esophagus without dysplasia to more advanced disease with minimal complications, as it limits damage to the surrounding healthy tissue and avoid mucosal perforation. Similar considerations may apply in gynecology and urology applications. Means to obtain images of the working area may include, for example, commercial fiberscope such Medit INC F2.4 (2.4 mm 45 degrees FOV, with 30,000 pixels) or Olympus LF-2 (designed for tracheal intubation) that can be inserted into 5 mm tubes and includes a 1.5 mm channel for easier aspiration/instillation of fluids, providing images with 90 degrees field of view from >3 mm so the fiber can be placed accordingly. As disclosed hereinabove, the hybrid catheter may be combined with a commercial endoscope, such as a gastroscope preferably such that has enhanced imaging capabilities such a narrow band imaging (NBI) to detect the pathological areas with higher resolution. For example, an Olympus GIF-H180J model (or equivalent) may be used, which has a 9.9 mm diameter at the distal end so the hybrid catheter can be attached to the walls in a manner that it can be conveniently introduced to the body. This enables four-way angulations (210° up, 90° down, and 100° right/left) a 140° field of view and close-up high resolution image can be obtained as close as 2 mm from the tissue, so the laser blade catheter can be attached accordingly to the tip of the scope (relatively advanced in few mm at the front).

There is provided herein, in accordance with some embodiments, a hybrid catheter having a tip section having optical fibers for transmitting (pulse) laser radiation and inner and/or outer walls having facet that are sharp enough to complete the cutting and debulking (extracting) of leads initiated by the laser but not sharp enough to work alone in order to maintain the procedure's safety. Using the hybrid catheter allows decreasing the requirements from the laser and thus enables use of small solid state lasers, in such way that when the debulking of the leads is not completed by laser cutting the tissue surrounding the leads is performed mechanically (by sharp wall(s) and/or by a blade).

Figure 13C:
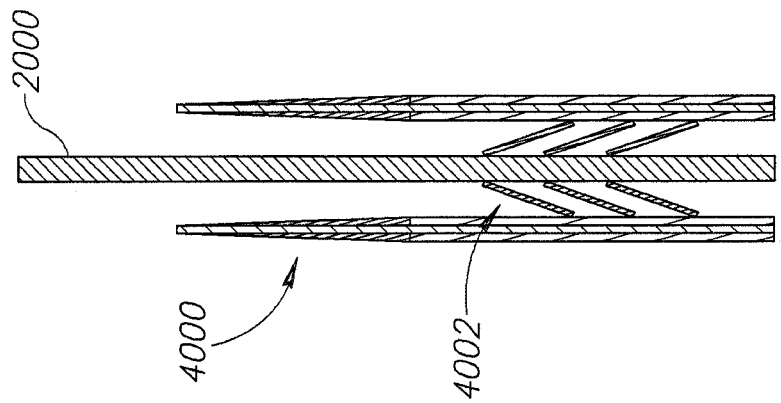
FIGS. 13A-13C show a cross section of a hybrid catheter over a lead to be extracted.
Figure 13B:
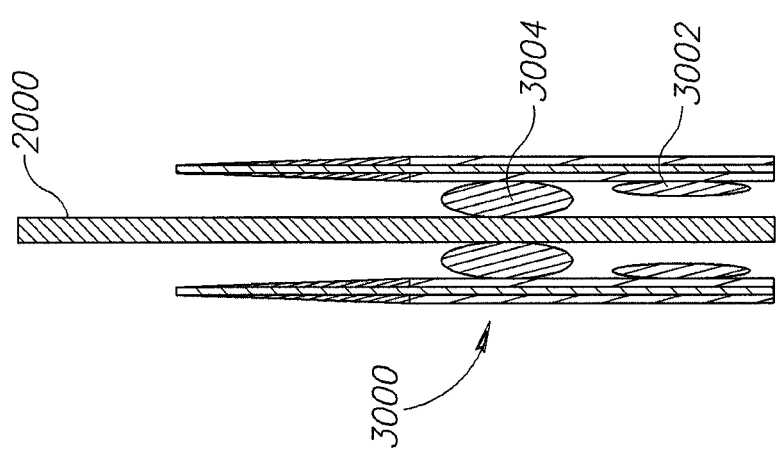
Figure 13A:
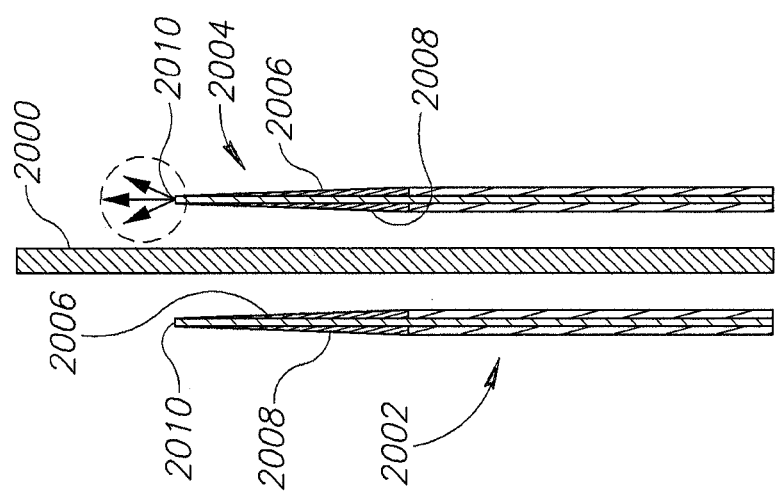

Reference is now made to FIGS. 13A-C, which show cross section illustrations of three types of a hybrid catheter for pacemaker and ICD (Implantable Cardioverter Defibrillator) lead extraction.

FIG. 13A shows a cross section of hybrid catheter 2002 over lead 2000 which is to be extracted. Catheter 2002 has a tip section 2004, typically having a circular cross section. Tip section 2004 comprises an inner wall 2006 and an outer wall 2008, at least one of which having a sharp (for example tapered) distal end which thus function like blades. Optical fiber(s) 2010 are located between inner wall 2006 and outer wall 2008 and are configured to transmit laser radiation through the distal end of tip section 2004 (as marked by the arrows). The laser radiation modifies (e.g., ablate, partially ablate, weaken, cut, etc.) the tissue surrounding the lead and thereby preparing the tissue for penetration of the sharp distal edge of inner wall 2006 and outer wall 2008, such that walls are configured to cut through the modified tissue and thereby detach lead 2000 from the tissue.

According to some embodiment, the catheter may include means to hold the lead in order to extract it from the body. These embodiment aim to replace a complicated process known in the art wherein a lead locking device is inserted (e.g. Spectranetics Lead Locking Device (LLD®)) and then another catheter used for laser ablation (Spectranetics SLS® II) is inserted. Two examples of means for holding and retracting the lead are schematically illustrated in FIGS. 13B and 13C, in accordance with some embodiments.

FIG. 13B shows a cross section of hybrid catheter 3000 over lead 2000 which is to be extracted. Catheter 3000 may be similar to catheter 2002, but further includes a "donut shaped" balloon (3002/3004) connected to an inner wall of hybrid catheter 3000. When hybrid catheter 3000 is penetrating through the tissue surroundings lead 2000 the balloon is deflated (3002). When hybrid catheter 3000 is pulled out in order to extract lead 2000 the balloon is inflated (3004) and "holds" lead 2000 and thus assist in its extraction.

FIG. 13C shows a cross section of hybrid catheter 4000 over lead 2000 which is to be extracted. Catheter 4000 may be similar to catheter 2002, but further includes "grabbing elements" 4002, configured to allow smooth penetration of catheter 4000 through the tissue surroundings lead 2000 but to hold lead 2000 in a predetermined force when moving outside. According to some embodiments, the catheter may include means to release this holding in cases there is a need to retract the catheter without the lead.

In the description and claims of the application, each of the words "comprise" "include" and "have", and forms thereof, are not necessarily limited to members in a list with which the words may be associated. In addition, where there are inconsistencies between this application and any document referenced or incorporated by reference, it is hereby intended that the present application controls.

What is claimed is:

1. A catheter for debulking of an undesired deposit from an inner surface of at least one of a blood vessel wall and a stent located in a blood vessel, said catheter having a tip section comprising a wall at an end of the tip section, the tip section having a central longitudinal axis, said tip section comprising:

circumferentially-directed laser optics comprising a plurality of optical fibers disposed within the wall and positioned parallel to said central longitudinal axis and configured to provide transmission of laser radiation, parallel to said central longitudinal axis from a distal end of said tip section to the undesired deposit, when in use; and a circular-action cutter, wherein said cutter is formed from a distal edge of the wall of said tip section or affixed to said distal end of said tip section's wall inwardly or outwardly to the plurality of optical fibers; and wherein said cutter is positioned outside an optical path of said laser radiation;

wherein said circumferentially-directed laser optics is configured to transmit laser radiation for ablating an area of the undesired deposit thereby preparing said area for penetration of said cutter; and wherein said cutter is configured to cut through said ablated area and thereby debulk at least a part of the undesired deposit.

2. The catheter of claim 1, wherein said tip section is cylindrical.

3. The catheter of claim 1, wherein said circumferentially-directed laser optics comprises a plurality of optical fibers embedded within a wall of the tip section.

4. The catheter of claim 3, wherein said plurality of optical fibers comprises one or more optical fibers having a proximal diameter larger than their distal diameter.

5. The catheter of claim 1, further comprising a light concentrator at a distal end of said tip section.

6. The catheter of claim 1, wherein said circular-action cutter comprises a blade rotatable along said tip section's wall, inwardly or outwardly to said laser optics.

7. The catheter of claim 1, wherein said laser is selected from the group consisting of: a pulsed laser, a solid state triple Nd:YAG laser, a pulse Thulium laser, a pulse Thulium fiber laser, an Er:YAG laser and a diode pump Holmium Fiber laser.

8. The catheter of claim 1, wherein said laser is selected from a fiber laser and a pulse laser, and wherein the laser is configured to emit laser in the range of 2.8-3 microns.

9. The catheter of claim 1, wherein said laser optics are configured to transmit laser radiation at a wavelength of 355 nm.

10. The catheter of claim 1, wherein said laser optics are configured to transmit laser radiation at 10 nsec pulses of 30-60 $mJ/mm^2$.

11. The catheter of claim 1, wherein said cutter is not sharp enough to debulk said undesired deposit without the ablation of the undesired deposit by said laser radiation, thereby avoiding potential perforation of the inner wall of the body cavity.

12. The catheter of claim 1, wherein said plurality of optical fibers and said cutter are configured to operate simultaneously.

13. The catheter of claim 6, wherein said cutter is affixed to said wall inwardly to the plurality of optical fibers.

* * * * *